(12) United States Patent
Snell et al.

(10) Patent No.: US 10,017,573 B2
(45) Date of Patent: *Jul. 10, 2018

(54) ANTI-αβTCR ANTIBODY

(75) Inventors: Daniel Snell, Thalwil (CH); Andreas Menrad, Ely (GB); Gina Lacorcia, Concord, MA (US); Srinivas Shankara, Shrewsbury, MA (US); Huawei Qiu, Westborough, MA (US); Clark Pan, Sudbury, MA (US); Benjamin Kebble, Zurich (CH)

(73) Assignee: GENZYME CORPORATION, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/241,099

(22) PCT Filed: Sep. 12, 2012

(86) PCT No.: PCT/EP2012/003819
§ 371 (c)(1),
(2), (4) Date: Nov. 18, 2014

(87) PCT Pub. No.: WO2013/037484
PCT Pub. Date: Mar. 21, 2013

(65) Prior Publication Data
US 2015/0099861 A1 Apr. 9, 2015

Related U.S. Application Data

(60) Provisional application No. 61/533,510, filed on Sep. 12, 2011.

(51) Int. Cl.
*A61K 39/395* (2006.01)
*C07K 16/28* (2006.01)

(52) U.S. Cl.
CPC ...... *C07K 16/2809* (2013.01); *C07K 16/2893* (2013.01); *C07K 2317/24* (2013.01); *C07K 2317/31* (2013.01); *C07K 2317/71* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2008/0038260 A1  2/2008  Ponath
2010/0190247 A1  7/2010  Lazar

FOREIGN PATENT DOCUMENTS

| EP | 0403156A1 A1 | 12/1990 |
|---|---|---|
| WO | 2004/099249 A2 | 11/2004 |
| WO | WO2006105021 A2 | 10/2006 |
| WO | WO2008086006 A2 | 7/2008 |
| WO | WO2010027797 A1 | 3/2010 |
| WO | WO2011109400 A2 | 9/2011 |

OTHER PUBLICATIONS

Sazinsky et al., PNAS, 2008, 105:51 20167-20172.*
Williams et al. ("Humanising Antibodies by CDR Grafting" in Chapter 21 of Antibody Engineering vol. 1, Kontermann and Dubel Eds., Springer-Verlag Berlin Heidelberg 2010, pp. 319-339).*
Al-Lazikani et al. (J. Mol. Biol. (1997) 273, 927-948).*
Giudicelli et al. (Cold Spring Harb Protoc. Jun. 1, 2001;2011(6), pp. 58-78).*
Andrew C.R. Martin, "Protein Sequence and Structure Analysis of Antibody Variable Domains" in Chapter 3 of Antibody Engineering vol. 2, Kontermann and Dubel Eds., Springer-Verlag Berlin Heidelberg 2010, pp. 33-51.*
North et al. (J. Mol. Biol. (2011) 406, 228-256).*
Sazinsky et al. (Proc Natl Acad Sci U S A. Dec. 23, 2008;105(51):20167-72 and Supplemental pp. 1-8).*
Feige et al., J. Mol. Biol. (2009) 391, 599-608.*
Krapp et al., J. Mol. Biol. (2003) 325, 979-989.*
Page et al. 'Biologics in Organ Transplantation'. 2012 Transplant International. European Society for Organ Transplantation. vol. 25 pp. 707-719.
Yoshino, Shin. Cleland, Leslie G. 'Depletion of Alpha-beta T Cells by a Monoclonal Antibody against the Alpha-beta T Cell Receptor Suppresses Established Adjuvant Arthritis, but not Established Collagen-induced Arthritis in Rats'. 1992 J. Exp. Med. vol. 175 pp. 907-915.
Yamagami et al. 'Suppression of Allograft Rejection with Anti-alpha-beta T Cell Receptor Antibody in Rat Corneal Transplantation'. 1999 Transplantation vol. 67 No. 4 pp. 600-604.
Heidecke et al. 'Alpha-beta T Cell Receptor-directed Therapy in Rat Allograft Recipients'. 1996 Transplantation vol. 61 No. 6 pp. 948-956.
Wright et al. 'Genetically Engineered Antibodies: Progress and Prospects'. 1992 Critical Reviews in Immunology vol. 12 No. 3-4 pp. 125-168.
Scharpf et al. 'Immunomodulation with Anti-alpha-beta T Cell Receptor Monoclonal Antibodies in Combination With Cyclosporine A Improves Regeneration in Nerve Allografts'. 2006 Microsurgery vol. 26 pp. 599-607.
Heidecke et al. 'Induction of Long-term Rat Renal Allograft Survival by Pretransplant T Cell Receptor Alpha-beta Targeted Therapy'. 1996 Transplantation vol. 61 No. 2 pp. 336-339.
Jung et al. 'Prevention and Therapy of Experimental Autoimmune Neuritis by an Antibody Against T Cell Receptors-alpha-beta'. 1992 Journal of Immunology vol. 148 No. 12 pp. 3768-3775.
Schorlemmer et al. 'Synergistic Effects of 15-Deoxyspergualin With Cyclosporine and the TCR-Targeted Monoclonal Antibody R73 to Induce Specific Unresponsiveness to Skin Allografts in Rats' 1995 Transplantation Proceedings vol. 27 No. 1 pp. 414-416.
International Search Report. PCT/EP2012/003819 dated Jun. 28, 2013.

(Continued)

*Primary Examiner* — Zachary S Skelding
(74) *Attorney, Agent, or Firm* — Lathrop Gage LLP; James H. Velema, Esq.

(57) ABSTRACT

The present invention relates to humanized monoclonal antibodies comprising the CDRs of murine antibody BMA031, which bind to the apTCR.CD3 complex and possess improved biological properties.

12 Claims, 26 Drawing Sheets

(56) References Cited

OTHER PUBLICATIONS

Shearman et al. 'Construction, Expression, and Characterization of Humanized Antibodies Directed Against the Human Alpha-beta T Cell Receptor'. 1991 Journal of Immunology vol. 147 No. 12 pp. 4366-4373.
Written Opinion of The International Searching Authority. PCT/EP2012/003819 dated Sep. 12, 2011.
Chan et al. (2010) "Therapeutic antibodies for autoimmunity and inflammation," The Journal of Immunology. 10:301-316.
Labrijn et al. (2008) "When binding is enough: nonactivating antibody formats," Curr. Opin. Immunol. 20:479-485.
Shields et al. (2001) "High Resolution Mapping of the Binding Site on Human IgG1 for FcyRl, FcyRll, FcyRlll, and FcRn and Design of IgG1 Variants with Improved Binding to the FcyR," J. Biol. Chem. 276:6591-6604.
Zhou et al. (2008) "Development of a simple and rapid method for producing non-fucosylated oligomannose containing antibodies with increased effector function," Biotechnol. Bioeng. 99:652-665.

\* cited by examiner

Human FcγRIIIa Binding

Fullscale: CD16a-Val158

Fullscale: CD16a-Phe158 zoomed:

zoomed:

○ Very little FcγRIIIa Binding by the mutants, H66 S298N/T299A/Y300S in particular.

A.

B.

C.

SEQUENCE LISTING

```
<160> NUMBER OF SEQ ID NOS: 24

<210> SEQ ID NO 1
<211> LENGTH: 120
<212> TYPE: PRT
<213> ORGANISM: Mus musculus

<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Lys Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Val Thr Lys Tyr Asn Glu Lys Phe
    50                  55                  60
```

```
Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val His Tyr Cys
                 85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ala
            115                 120

<210> SEQ ID NO 2
<211> LENGTH: 106
<212> TYPE: PRT
<213> ORGANISM: Mus musculus

<400> SEQUENCE: 2

Gln Ile Val Leu Thr Gln Ser Pro Ala Ile Met Ser Ala Ser Pro Gly
 1               5                  10                  15

Glu Lys Val Thr Met Thr Cys Ser Ala Thr Ser Ser Val Ser Tyr Met
                 20                  25                  30

His Trp Tyr Gln Gln Lys Ser Gly Thr Ser Pro Lys Arg Trp Ile Tyr
             35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys
            100                 105

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      EuCIV3 Heavy chain variable domain polypeptide

<400> SEQUENCE: 3

Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Lys Phe Thr Ser Tyr
                 20                  25                  30

Val Met His Trp Val Lys Gln Ala Pro Gly Gln Gly Leu Glu Trp Ile
             35                  40                  45

Gly Tyr Ile Asn Pro Tyr Asn Asp Val Thr Lys Tyr Asn Glu Lys Phe
 50                  55                  60

Lys Gly Lys Ala Thr Leu Thr Ala Asp Glu Ser Thr Asn Thr Ala Tyr
 65                  70                  75                  80

Met Glu Leu Ser Ser Leu Arg Ser Glu Asp Thr Ala Val His Tyr Cys
                 85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
            115                 120
```

```
<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      EuCIV3 Light chain variable domain polypeptide

<400> SEQUENCE: 4

Asp Ile Gln Met Thr Gln Ser Pro Ser Thr Leu Ser Ala Ser Val Gly
1               5                   10                  15

Asp Arg Val Thr Met Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ala Arg Phe Ile Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 5
<211> LENGTH: 120
<212> TYPE: PRT
<213> ORGANISM: Artificial Sequence
<220> FEATURE:
<223> OTHER INFORMATION: Description of Artificial Sequence: Synthetic
      HEBE1 Heavy chain variable domain polypeptide

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Lys Phe Thr Ser Tyr
            20                  25                  30

Val Met His Trp Val Lys Gln Ala Pro Gly Lys Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Lys Ala Thr Leu Ser Arg Asp Asn Ser Lys Asn Thr Leu Tyr
65                  70                  75                  80

Leu Gln Met Asn Ser Leu Arg Ala Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      HEBE1 Light chain variable domain polypeptide
```

<400> SEQUENCE: 6

Asp Ile Gln Met Thr Gln Ser Pro Ser Thr Leu Ser Ala Ser Val Gly
1               5                   10                  15

Asp Arg Val Thr Met Thr Cys Ser Ala Thr Ser Ser Val Ser Tyr Met
            20                  25                  30

His Trp Tyr Gln Gln Lys Pro Gly Lys Ala Pro Lys Arg Trp Ile Tyr
        35                  40                  45

Asp Thr Ser Lys Leu Ala Ser Gly Val Pro Ala Arg Phe Ile Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      HEBE1 H10 Heavy chain variable domain polypeptide

<400> SEQUENCE: 7

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Lys Phe Thr Ser Tyr
            20                  25                  30

Val Met His Trp Val Lys Gln Ala Pro Gly Lys Gly Leu Glu Trp Ile
        35                  40                  45

Gly Tyr Ile Asn Pro Tyr Asn Asp Val Thr Lys Tyr Asn Glu Lys Phe
    50                  55                  60

Lys Gly Lys Ala Thr Leu Ser Arg Asp Asn Ser Lys Asn Thr Leu Tyr
65                  70                  75                  80

Leu Gln Met Asn Ser Leu Arg Ala Glu Asp Thr Ala Val His Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: Description of Artificial Sequence: Synthetic
      GL1BM Heavy chain variable domain polypeptide

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Arg Leu Glu Trp Met
        35                  40                  45

```
Gly Tyr Ile Asn Pro Tyr Asn Asp Val Thr Lys Tyr Asn Glu Lys Phe
        50                  55                  60

Lys Gly Lys Ala Thr Ile Thr Arg Asp Thr Ser Ala Asn Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: Synthetic
      GL1BM Light chain variable domain polypeptide

<400> SEQUENCE: 9

Glu Ile Val Leu Thr Gln Ser Pro Ala Thr Leu Ser Leu Ser Pro Gly
 1               5                  10                  15

Glu Arg Ala Thr Leu Ser Cys Ser Ala Thr Ser Ser Val Ser Tyr Met
                 20                  25                  30

His Trp Tyr Gln Gln Lys Pro Gly Gln Ala Pro Arg Arg Trp Ile Tyr
             35                  40                  45

Asp Thr Ser Lys Leu Ala Ser Gly Val Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Trp Ser Ser Asn Pro Leu Thr
                 85                  90                  95

Phe Gly Gly Gly Thr Lys Val Glu Ile Lys
            100                 105

<210> SEQ ID NO 10
<211> LENGTH: 329
<212> TYPE: PRT
<213> ORGANISM: Homo sapiens

<400> SEQUENCE: 10

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
            115                 120                 125
```

```
Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 11
<211> LENGTH: 327
<212> TYPE: PRT
<213> ORGANISM: Artificial Sequence
<220> FEATURE:
<223> OTHER INFORMATION: Description of Artificial Sequence: Synthetic
      HuIgG4 agly Fc polypeptide

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160
```

Gly Val Glu Val His Asn Ala Lys Thr Lys Pro Arg Glu Glu Gln Phe
            165                 170                 175

Gln Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
        245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      HEBE1 H66 Heavy chain variable domain polypeptide

<400> SEQUENCE: 12

Glu Val Gln Leu Leu Gln Ser Gly Gly Gly Leu Val Gln Pro Gly Gly
1               5                   10                  15

Ser Leu Arg Leu Ser Cys Ala Ala Ser Gly Tyr Lys Phe Thr Ser Tyr
            20                  25                  30

Val Met His Trp Val Arg Gln Ala Pro Gly Lys Gly Leu Glu Trp Val
        35                  40                  45

Gly Tyr Ile Asn Pro Tyr Asn Asp Val Thr Lys Tyr Asn Glu Lys Phe
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      HEBE1 H71 Heavy chain variable domain polypeptide

<400> SEQUENCE: 13

Glu Val Gln Leu Leu Glu Ser Gly Gly Gly Leu Val Gln Pro Gly Gly
1               5                   10                  15

Ser Val Arg Leu Ser Cys Ala Ala Ser Gly Tyr Lys Phe Thr Ser Tyr
            20                  25                  30

Val Met His Trp Val Arg Gln Ala Pro Gly Lys Gly Leu Glu Trp Val
        35                  40                  45

Gly Tyr Ile Asn Pro Tyr Asn Asp Val Thr Lys Tyr Asn Glu Lys Phe
    50                  55                  60

Lys Gly Arg Phe Thr Leu Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Tyr Asp Tyr Asp Gly Phe Val Tyr Trp Gly Gln
            100                 105                 110

Gly Thr Leu Val Thr Val Ser Ser
        115                 120

<210> SEQ ID NO 14
<211> LENGTH: 106
<212> TYPE: PRT
<213> ORGANISM: Artificial Sequence
<220> FEATURE:
<223> OTHER INFORMATION: Description of Artificial Sequence: Synthetic
      GL1BM VK43 Light chain variable domain polypeptide

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Leu Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      GL1BM VH28 Heavy chain variable domain polypeptide

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Lys Gln Ala Pro Gly Gln Gly Leu Glu Trp Ile
        35                  40                  45

Gly Tyr Ile Asn Pro Tyr Asn Asp Val Thr Lys Tyr Asn Glu Lys Phe
            50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      GL1BM VH31 Heavy chain variable domain polypeptide

<400> SEQUENCE: 16

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Lys Phe Thr Ser Tyr
                20                  25                  30

Val Met His Trp Val Arg Gln Ala Pro Gly Gln Gly Leu Glu Trp Ile
            35                  40                  45

Gly Tyr Ile Asn Pro Tyr Asn Asp Val Thr Lys Tyr Asn Glu Lys Phe
            50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 17
<211> LENGTH: 98
<212> TYPE: PRT
<213> ORGANISM: Homo sapiens

<400> SEQUENCE: 17

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 18
<211> LENGTH: 98
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 19
<211> LENGTH: 95
<212> TYPE: PRT
<213> ORGANISM: Homo sapiens

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
     GL1BM VHdeltaS polypeptide

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
            20                  25                  30

Val Met His Trp Val Arg Gln Ala Pro Gly Gln Arg Leu Glu Trp Met
        35                  40                  45

Gly Tyr Ile Asn Pro Tyr Asn Asp Val Thr Lys Tyr Asn Glu Lys Phe
    50                  55                  60

Lys Gly Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Ser Tyr Tyr Asp Tyr Asp Gly Phe Val Tyr Trp Gly Gln
        100                 105                 110

Gly Thr Leu Val Thr Val Ser Ser
        115                 120

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      GL1BM VK1 polypeptide

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: Description of Artificial Sequence: Synthetic
      GL1BM VK27 polypeptide

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Phe Thr Leu Thr Ile Ser Ser Met Glu Pro Glu
65                  70                  75                  80

Asp Phe Ala Val Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 23
<211> LENGTH: 120
<212> TYPE: PRT
<213> ORGANISM: Artificial Sequence

```
<220> FEATURE:
<223> OTHER INFORMATION: Description of Artificial Sequence: Synthetic
      GL1BM VHdeltaS VH11 polypeptide

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Val Thr Lys Tyr Asn Glu Lys Phe
    50                  55                  60

Lys Gly Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      GL1BM VHdeltaS VH15 polypeptide

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Lys Phe Thr Ser Tyr
                20                  25                  30

Val Met His Trp Val Lys Gln Ala Pro Gly Gln Gly Leu Glu Trp Ile
            35                  40                  45

Gly Tyr Ile Asn Pro Tyr Asn Asp Val Thr Lys Tyr Asn Glu Lys Phe
    50                  55                  60

Lys Gly Lys Ala Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Asp Tyr Asp Gly Phe Val Tyr Trp Gly Gln
                100                 105                 110

Gly Thr Leu Val Thr Val Ser Ser
            115                 120
```

ANTI-αβTCR ANTIBODY

RELATED APPLICATIONS

This application is a 35 U.S.C. § 371 filing of International Application No. PCT/EP2012/003819, filed Sep. 12, 2012, which claims priority to U.S. Patent Application No. 61/533,510, filed Sep. 12, 2011. The entire contents of each are incorporated herein by reference.

SEQUENCE LISTING

The instant application contains a Sequence Listing which has been submitted electronically in ASCII format and is hereby incorporated by reference in its entirety. Said ASCII copy, created on Dec. 9, 2014, is named 5548095A9-096US_SL.txt and is 30,786 bytes in size.

The present invention relates to an antibody specific for the alpha beta T cell receptor (αβTCR). In particular, the invention relates to a humanized anti-αβTCR antibody, which is derived from the murine monoclonal antibody BMA031, and the use of said humanized antibody in immunosuppressive therapy.

INTRODUCTION

The use of immunosuppressive agents in autoimmune diseases and organ transplant therapy is well documented; however the process is far from optimal. Toxicity, opportunistic infections, cytokine storm and increased risk of cancer are prevalent in patients treated with these agents. The use of biologics in this arena has improved patient outcome to some degree yet these side effects remain evident.

The use of polyclonal antisera against lymphocytes is well known for the purpose of immunosuppression. However, antisera are labor-intensive to produce, show properties which vary between batches, and the specificity which can be obtained using polyclonal antisera is limited.

Monoclonal antibody production by hybridoma technology was first described by Köhler and Milstein (*Nature* 256:495-497 (1975)). As compared to polyclonal antisera, monoclonal antibodies (mAbs) are more specific, and have more consistent properties. mAbs have been most frequently and successfully used for immunosuppressive therapy in clinical organ transplantation. However, most mAbs used as immunosuppressive agents for treating autoimmune diseases and in transplant patients have a broad immunosuppressive capacity, thus undesirably influencing functions of a wide spectrum of immune cells, presumably not all involved in graft rejection.

Mouse monoclonal antibodies against T cell surface receptor antigens were first produced in 1979 using hybridoma technology (Kung et al. (1979) *Science* 206:347-349). Of the three monoclonal antibodies discovered by Kung et al., one antibody designated muromonab-CD3 (OKT3) had defined specificity to the CD3 receptor of the T cell, reacting with more that 95% of peripheral mature T cells without affecting immature thymocytes. Binding of OKT3 to the CD3 complex causes internalization of the CD3 receptor and loss of CD3 positive cells from the periphery. Successful OKT3 treatment is associated with a prompt decline in CD3 positive T cells from approximately 60% to less than 5%.

OKT3 has been extensively used for the treatment of patients undergoing acute allograft rejection after kidney transplantation (Russell, P. S., Colvin, R. B., Cosimi, A. B. (1984) *Annu. Rev. Med.* 35:63 and Cosimi, A. B., Burton, R. C., Colvin, R. B. et al. (1981) *Transplantation* 32:535). Moreover, OKT3 and rabbit complement were used for purging mature T cells from donor marrow to prevent acute graft versus host disease (GVHD) in allogeneic bone marrow transplantation (Prentice, H. G., Blacklock, H. A., Janossy, G. at al. (1982) *Lancet* 1:700 and Blacklock, H. A., Prentice, H. G., Gilmore, M. J. et al. (1983) *Exp. Hematol.* 11:37). Whereas OKT3 treatment seems to be effective in the prevention of GVHD in allogeneic bone marrow transplantation for acute leukemia, a combined in vitro/in vivo treatment with OKT3 failed to prevent GVHD during therapy for severe combined immunodeficiency (Hayward, A. R. et al. (1982) *Clin. Lab. Observ.* 100:665). Treatment of T cells with OKT3 elicits several responses inconsistent with immune suppression including T cell activation, production of immune mediators and T3-modulation. The T3-antigen complex recognized by CD3-mAbs (e.g., OKT3) is postulated to play a crucial role during T cell activation. Alpha/beta T lymphocytes recognize peptide—MHC ligands by means of a multimeric protein ensemble termed the αβ T cell antigen receptor (TCR).CD3 complex. This structure is composed of a variable αβ TCR dimer which binds antigens and three invariant dimers (CD3γε, δε and ζζ) which are involved in TCR.CD3 surface transport, stabilization and signal transduction. The alpha beta T cell receptor (αβTCR) is expressed on the majority (approx. 95%) of T cells and has a critical role in T cell activation via engagement of antigen displayed on MHC. The remaining 5% of cells are gamma delta T cell receptor (γδTCR) positive. The γδTCR positive cell population plays an important role in the innate immune response in defense against opportunistic infections of bacterial, viral and fungal origin. Gamma delta T cells do not play a role in graft rejection in transplantation. Therefore, targeting the αβTCR positive cell population and sparing the γδTCR positive population should allow for significant therapeutic efficacy whilst maintaining a baseline immune protection against opportunistic infections.

The mouse IgG2b monoclonal antibody BMA031 (Borst et al. (November 1990) *Hum. Immunol.* 29(3):175-88; EP0403156) is specific for the common determinant on the TCR alpha/beta/CD3 complex, and does not bind to the gamma-delta TCR. BMA031 is highly immunosuppressive and is capable of inducing apoptosis of activated T cells via a mechanism of activation-induced cell death (AICD) (Wesselborg et al. (May 1993) *J. Immunol.* 150(10): 4338-4345). In vitro it inhibits a mixed lymphocyte reaction and it has shown preliminary clinical efficacy in prevention of graft rejection in a number of solid organ transplant scenarios as well as the treatment of acute graft versus host disease (aGVHD) (Kurrle et al. (February 1989) *Transplant Proc.* 21(1): 1017-1019). BMA031 does not engage human Fc gamma receptors (FcγR) in the majority of the human population (approximately 10% of human possess FcγRs which do bind to mouse IgG2b isotype). As such the antibody does not cause T cell activation via cross-linking of the T cell receptor and, therefore, it does not induce T cell activation or the associated cytokine release. In this regard its profile is highly preferable over that of OKT3. However, BMA031 is a murine antibody and, as such, is not suitable for repeat dosing in human subjects in view of the human anti-mouse antibody (HAMA) response elicited therein.

Several humanized versions of BMA031 have been described (see, EP 0403156; also Shearman et al., (1991) *J. Immunol.* 147:4366-4373). As noted in EP0403156, mere CDR grafting was not successful in retaining antigen binding. One clone with significant framework modifications, EUCIV3, successfully bound to T cells; however, as noted in EP0403156, binding to the αβTCR is not as effective as the parent BMA031 antibody as determined by flow cytometry competition assays. We have also shown that the ability of EuCIV3 to inhibit an in vitro immune response is significantly reduced as compared to BMA031 (see, FIG. 2). In addition EuCIV3 was originally generated on a wild-type human IgG1 or IgG4 backbone which still retains FcγR binding. These humanized antibodies therefore allowed for T cell activation, proliferation and the concomitant cytokine release and as such were significantly different to the original properties of BMA031.

The modification of antibody glycosylation is known in the art. For example, it is known that aglycosylated antibodies can have extensively modified functionality; see, Boyd et al. (1996) Mol. Immunol. 32:1311-1318. However, aglycosylated forms of humanized BMA031, or derivatives with modified glycosylation patterns, have previously not been described.

There is a need in the art, therefore, for an anti-αβTCR humanized antibody which improves on the binding properties of EUCIV3 and advantageously retains the immunosuppressive and non-T cell-activatory properties of BMA031.

SUMMARY OF THE INVENTION

In a first aspect, there is provided a humanized monoclonal antibody which comprises the CDRs of BMA031, and retains the binding affinity of BMA031 for its cognate antigen. In a first embodiment, said humanized antibody comprises a heavy chain variable region comprising the CDRs set forth in SEQ ID NOs: 7, 12 or 13 and the human IGH3-23 framework set forth in SEQ ID NO: 17, wherein framework position 6 is a donor residue; in an alternative embodiment, framework position 18 is a donor residue. Optionally, framework positions 49 and/or 69 are donor residues.

In a second embodiment, the humanized monoclonal antibody comprises a heavy chain variable region comprising the CDRs set forth in SEQ ID NOs: 15 or 16 and the human IGHV1-3*01 framework set forth in SEQ ID NO: 18, wherein one or more of framework positions 38, 44 and/or 48 is a donor residue; in an alternative embodiment, framework positions 44 and 48 are donor residues.

In a third embodiment, the humanized monoclonal antibody comprises a light chain variable region comprising the CDRs set forth in SEQ ID NO: 14 and the human IGKV3-11*01 framework set forth in SEQ ID NO: 19, wherein framework positions 70 and/or 71 are donor residues. Optionally, position 46 is a donor residue.

Examples of antibodies according to the first embodiment include antibodies which comprise a heavy chain variable region selected from the heavy chains comprising the sequences set forth in SEQ ID NO: 7, SEQ ID NO: 12 and SEQ ID NO: 13, and a light chain variable region sequence comprising the sequence as set forth in SEQ ID NO: 14.

Examples of antibodies according to the second embodiment include antibodies which comprise a heavy chain variable region selected from the heavy chains comprising the sequences set forth in SEQ ID NO: 15 and SEQ ID NO: 16, and a light chain variable region comprising the sequence as set forth in SEQ ID NO: 14. The humanized antibodies according to the described embodiments are humanized versions of the BMA031. Their primary structures differ from that of the humanized antibody EuCIV3, which has decreased binding to the αβTCR as compared to BMA031.

In the sequence listing, CDRs are indicated by means of annotation or underlining. Frameworks are all sequences outside of the CDRs, which are defined according to the "Kabat" numbering system and extended, where applicable, by use of "IMGT" CDR definition. If a framework residue is not indicated to be changed to match a donor sequence, it will ordinarily be understood to be an acceptor residue.

The humanized antibodies may comprise a constant region. In one embodiment, the constant region is of human origin.

The humanized antibodies of the invention may be further modified by Fc engineering. Immunoglobulins are liable to cross-link Fcγ receptors, which can lead to constitutive T cell activation for anti-T cell antibodies. In order to avoid Fcγ cross-linking, antibodies can be modified to remove the Fc region, such as by the generation of Fab or Fv fragments; however, truncated immunoglobulins lack beneficial effector functions and exhibit a lower serum half-life. Therefore, the Fc region of the humanized antibody can be modified to prevent Fcγ cross-linking. Exemplary techniques include generation of aglycosylated immunoglobulins, for instance by modification of the Fc region by an N297Q mutation. Immunoglobulins which fail to bind Fcγ are also described by Armour et al., (1999) Eur. J. Immunol. 29:2613-2624. The modification effected to IgG1 is known as the Δab modification, and consists in a combination of the Δa mutation, in which IgG residues are substituted at positions 327, 330 and 331, and IgG2 residues substituted at positions 233-236, and the Δb mutation, in which residue 236 is deleted. In another embodiment, the glycosylation pattern of antibodies according to the invention can be modified.

In one embodiment, the antibody comprised one or more of mutations S298N, T299A and Y300S.

In embodiments, the antibody comprises two or more of mutations N297Q, S298N, T299A and Y300S. For example, there is provided a humanized antibody comprising the multiple mutations N297Q/S298N/Y300S, S298N/T299A/Y300S or S298N/Y300S.

In a second aspect, there is provided a humanized monoclonal antibody which comprises the CDRs of BMA031, and retains the T cell suppression properties of BMA031. Said humanized antibody preferably comprises a heavy chain variable region having the amino acid sequence set forth in SEQ ID NOs: 12, 13, 15 or 16 and a light chain variable region comprising the amino acid sequence set forth in SEQ ID NO: 14.

In a third aspect, there is provided a nucleic acid encoding at least a heavy chain variable region of a humanized monoclonal antibody according to the preceding aspects of the described embodiments. The nucleic acid may encode variable and constant regions of the humanized antibody. Heavy and light chains may be encoded on separate nucleic acids or on the same nucleic acid molecule.

According to a fourth aspect, there is provided a cell which expresses a nucleic acid according to the preceding aspect. The cell is, for example, a cell adapted to express antibody molecules in culture. The nucleic acid may include signal sequences and/or other sequences or modifications which are required for, or which modulate, expression of the antibody molecule in the cell, and/or secretion of the antibody molecule from the cell.

In a further embodiment, a humanized antibody is provided as described in the foregoing aspects, for use in suppressing a T cell mediated response in a subject.

For example, the T cell mediated response can be involved in a condition selected from tissue transplantation, including solid organ transplant and composite tissue transplant, tissue grafting, multiple sclerosis and type 1 diabetes.

Moreover, another embodiment provides a method for treating a subject suffering from a condition involving an aberrant T cell mediated response comprising administering to a subject in need thereof a pharmaceutically effective dose of an antibody according to the described embodiments.

Humanized non-activatory anti-αβTCR antibodies which do not induce cytokine release have thus been generated which are capable of selective modulation of the αβTCR and of inducing apoptosis of activated αβTCR positive T cells. These antibodies have been generated for use as immunosuppressive agents in T cell mediated diseases. These antibodies have been generated through humanization of a mouse anti-αβTCR antibody BMA031 and by Fc-engineering of the humanized antibodies to prevent engagement of Fc gamma receptors. The antibodies according to the described embodiments retain the binding affinity of BMA031, unlike the humanized versions of BMA031 available in the art. Further, as shown in in vitro education assays, the immunosuppressive properties of antibodies according to the described embodiments are superior to those of BMA031. Moreover, unlike the humanized BMA031 antibodies of the prior art, the antibodies according to the described embodiments do not induce cytokine release in normal PBMC.

In accordance with a fifth aspect, there is provided an antibody comprising a modified Fc, in which said modified Fc comprises a modified glycosylation pattern which reduces FcγR receptor binding, comprising one or more of mutations S298N, T299A and Y300S.

In one embodiment, the antibody comprises two or more of mutations N297Q, S298N, T299A and Y300S.

In embodiments, the antibody comprises the multiple mutations N297Q/S298N/Y300S, S298N/T299A/Y300S or S298N/Y300S.

For example, the antibody may be an antibody as described in preceding aspects of the invention.

According to a sixth aspect, there is provided a multispecific antibody comprising at least a heavy chain of a first binding domain as described in the preceding aspects of the invention, and a second binding domain specific for a tumor-specific antigen.

In one embodiment, the first binding domain comprises a heavy chain according to the second aspect of the invention.

The multispecific antibody can comprise many different conformations; in one embodiment, it comprises an anti-TCR/CD3 scFv and an anti-tumor scFv.

In one embodiment, the multispecific antibody is bispecific.

Competition of binding of PE-labeled BMA031 antibody by BMA031 MoIgG2b, BMA031 HuIgG1 and EuCIV3 HuIgG1 antibodies. EuCIV3 has a decreased potency compared to BMA031.

Figure 2:
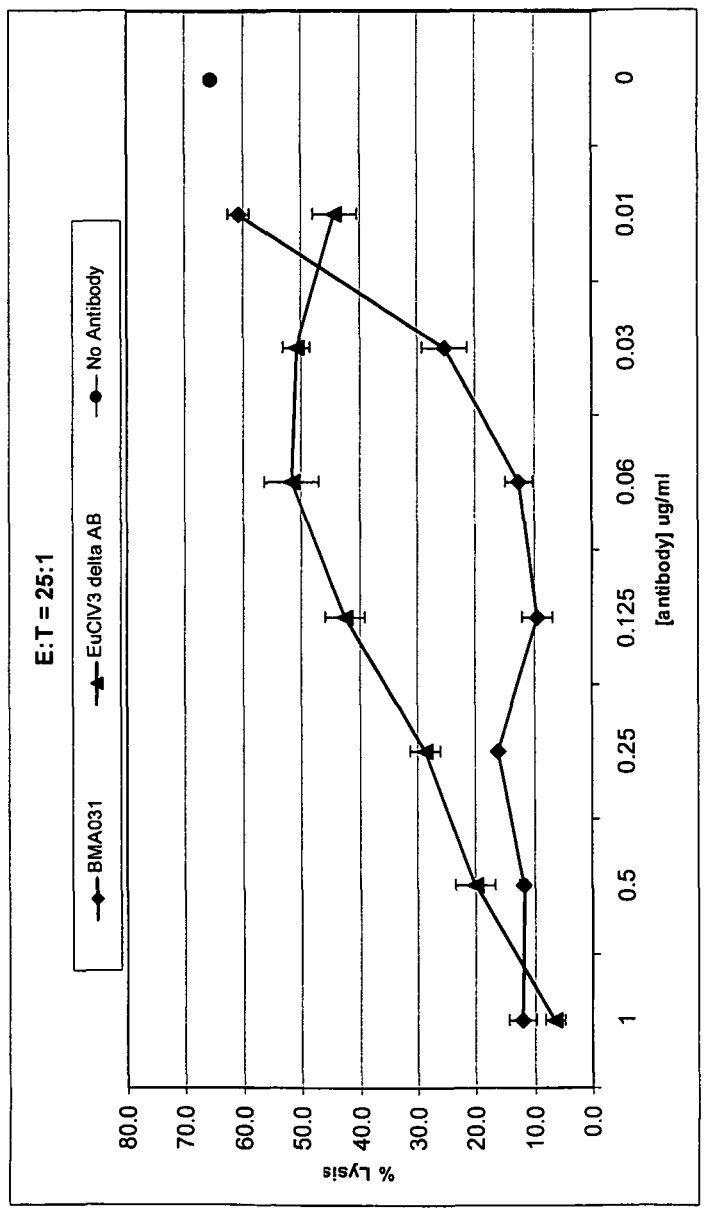

FIG. 2. EuCIV3 is less potent than BMA031 in an in vitro education (IVE) assay.

Plot showing loss of performance of EuCIV3 humanized antibody in biological assay when compared to parent BMA031 antibody. CD8+ T cells were treated with anti-αβTCR antibodies at various concentrations (x-axis) and co-cultured with autologous dendritic cells pulsed with the CMV peptide 495-503 (pp65) for seven days.

Figure 3:
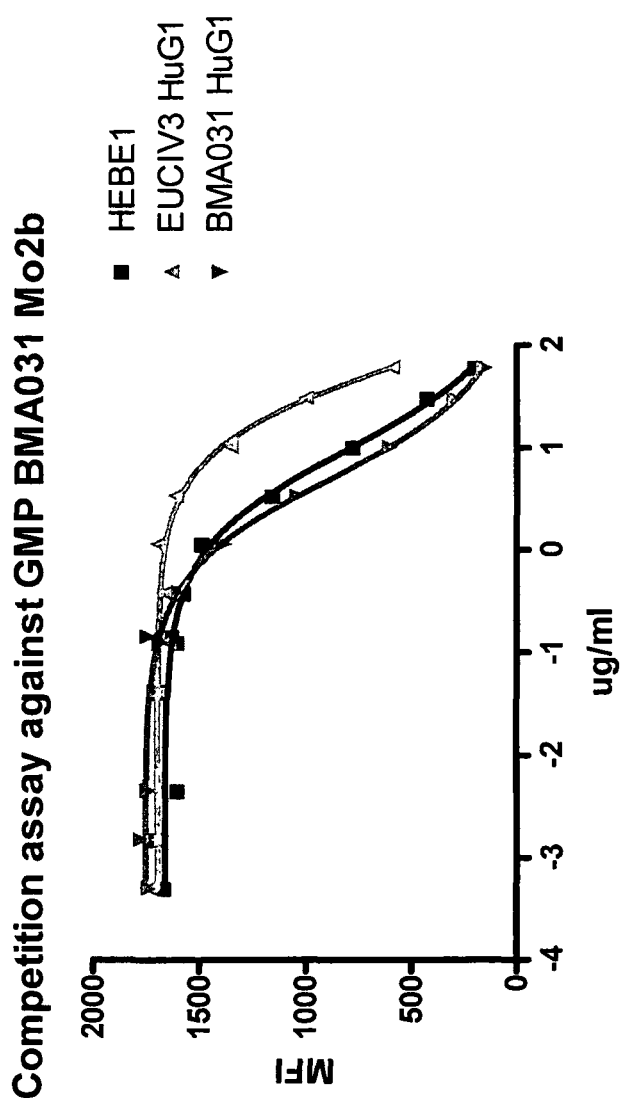

FIG. 3. HEBE1 binds αβTCR comparably to BMA031 in a competition assay.

Competition of binding of PE-labeled BMA031 antibody by BMA031 HuIgG1, HEBE1 HuIgG1 and EuCIV3 HuIgG1 antibodies. EuCIV3 has a decreased potency compared to BMA031 and HEBE1.

Figure 4:
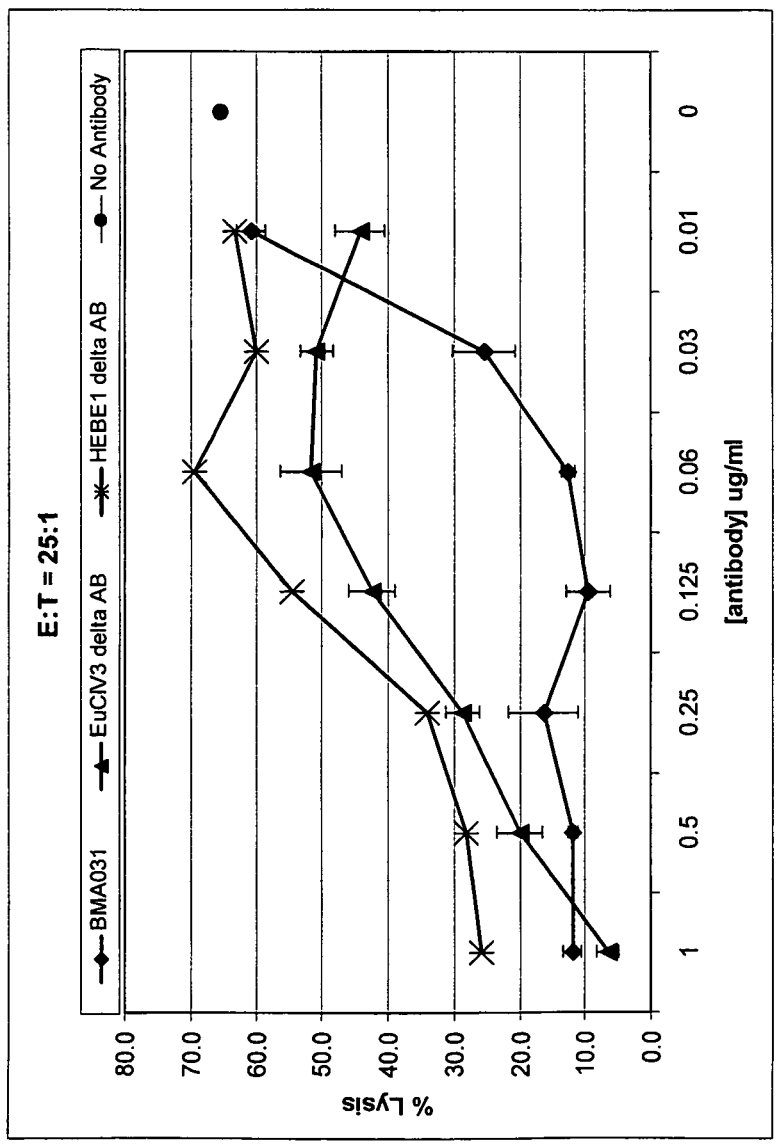

FIG. 4. HEBE1 has similar potency to EuCIV3 in an in vitro education (IVE) assay.

The IVE assay was performed as described in respect of FIG. 2.

Figure 5:
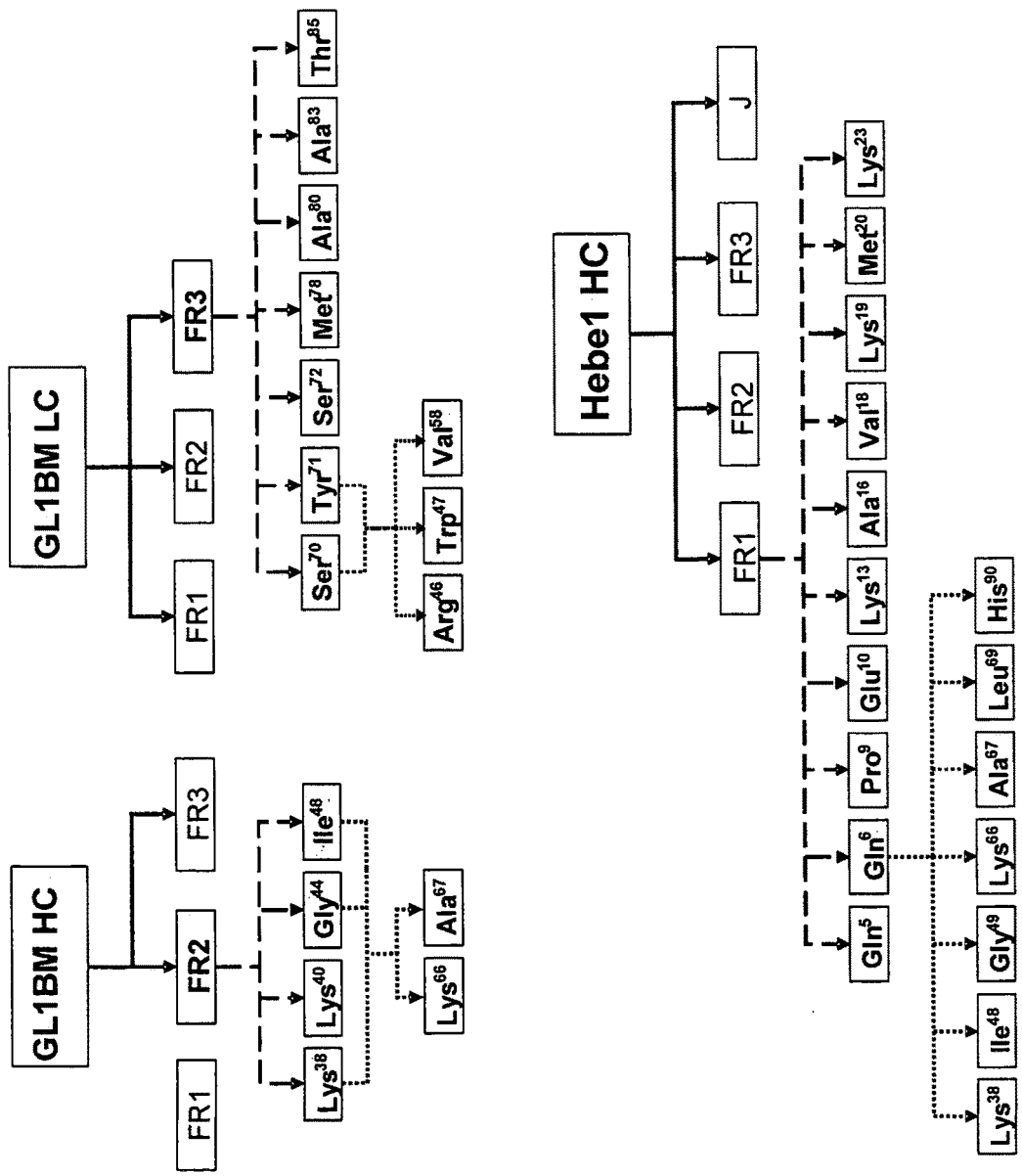

FIG. 5. Schematic showing iterative rounds of mutagenesis of anti-αβTCR variable domains.

Framework in shaded box depicts the FR region where certain mouse residues lie. Shaded residues in first row of mutations are the mouse amino acids that are useful to maintain off-rate. Shaded residues in second row of mutations are the mouse residues surrounding the CDR regions which were retained during the final germlining process.

Figure 6:
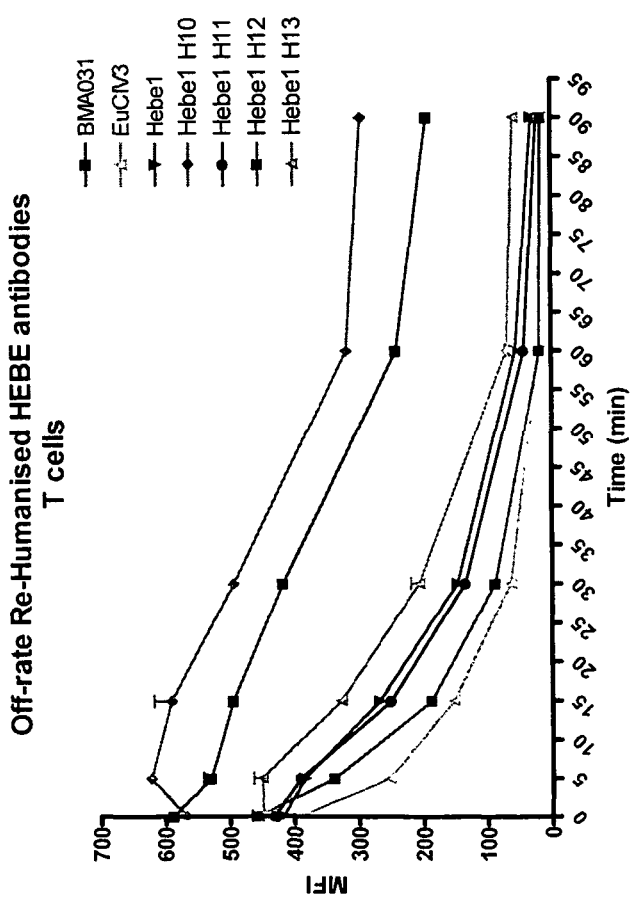

FIG. 6. Optimized humanized antibody has improved off-rate compared to BMA031.

The kinetics of antibody dissociation from αβTCR on T cells was measured by flow cytometry. BMA031 had a better off-rate compared to EuCIV3 and HEBE1. By optimizing the binding domain of HEBE1 we were able to improve the off-rate of HEBE1.H10 compared to BMA031.

Figure 7:
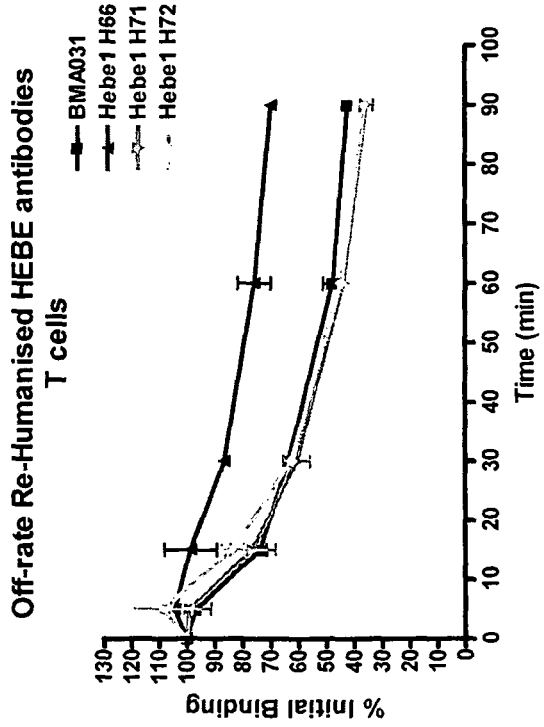

FIG. 7. Optimized humanized antibody has improved off-rate compared to BMA031.

The kinetics of antibody dissociation from αβTCR on T cells was measured by flow cytometry. By optimizing the binding domain of HEBE1 we were able to improve the off-rate of HEBE1.H66 compared to BMA031.

Figure 8:
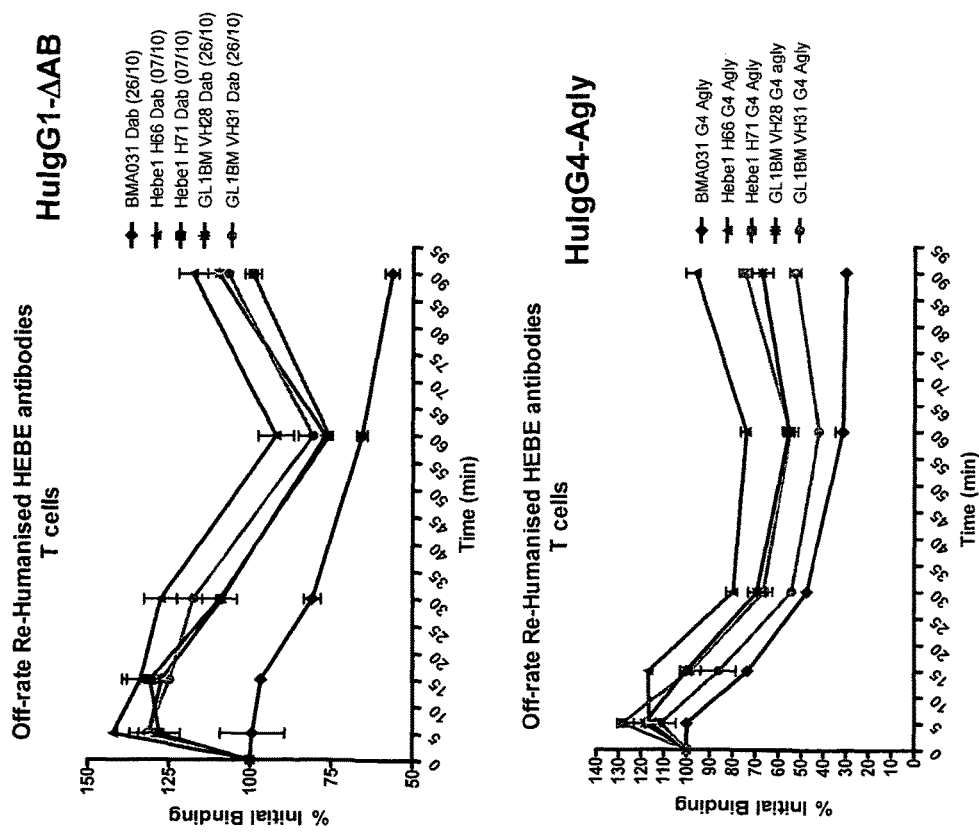

FIG. 8. Optimized humanized antibody has improved off-rate compared to BMA031 in both Δab and aglycosylated formats.

The kinetics of antibody dissociation from αβTCR on T cells was measured by flow cytometry.

Figure 9:
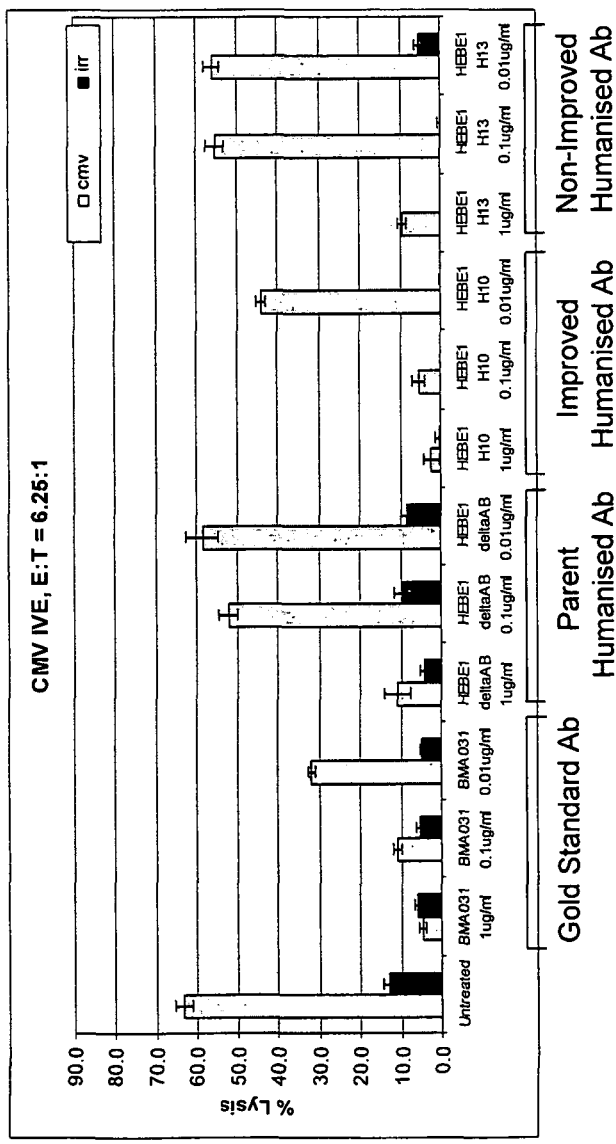

FIG. 9. Optimization of HEBE1 leads to equivalent functionality as BMA031.

IVE assay as described in FIG. 4. BMA031 inhibited education of CD8+ T cells, as they were unable to lyse specific targets in a dose dependent manner. The parental humanized antibody, HEBE1, was not as potent as BMA031 and was able to only inhibit education at the highest dose (similar results observed with a second non-improved humanized Ab, HEBE1 H13). Further improvements were made to the humanized antibody, HEBE1 H10, which had equivalent potency to BMA031 in this assay.

Figure 10:
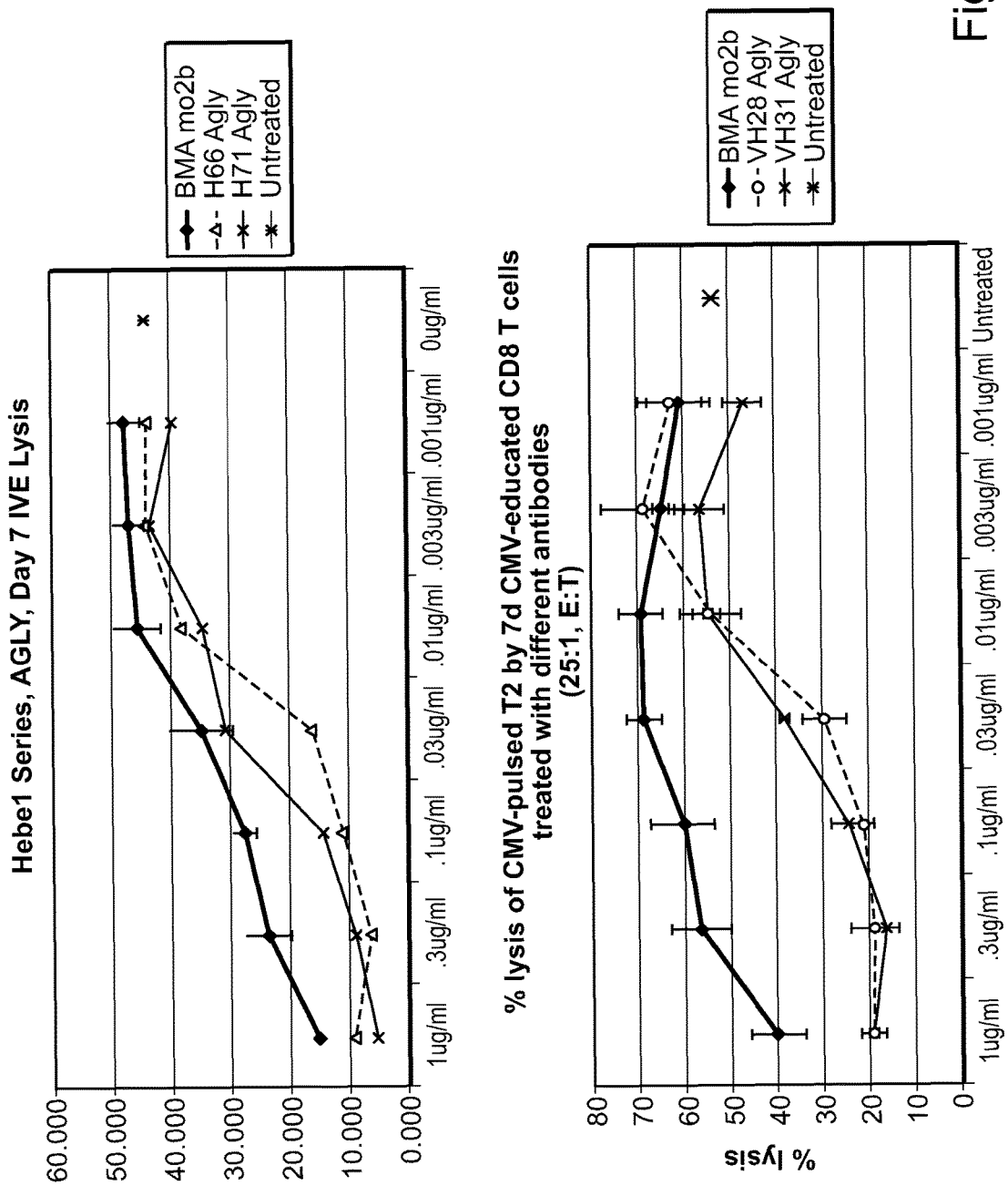

FIG. 10. IVE data with anti-αβTCR antibodies.

Both HEBE1 and GL1 BM series antibodies showed improvements in IVE results in comparison with BMA031.

Figure 11:
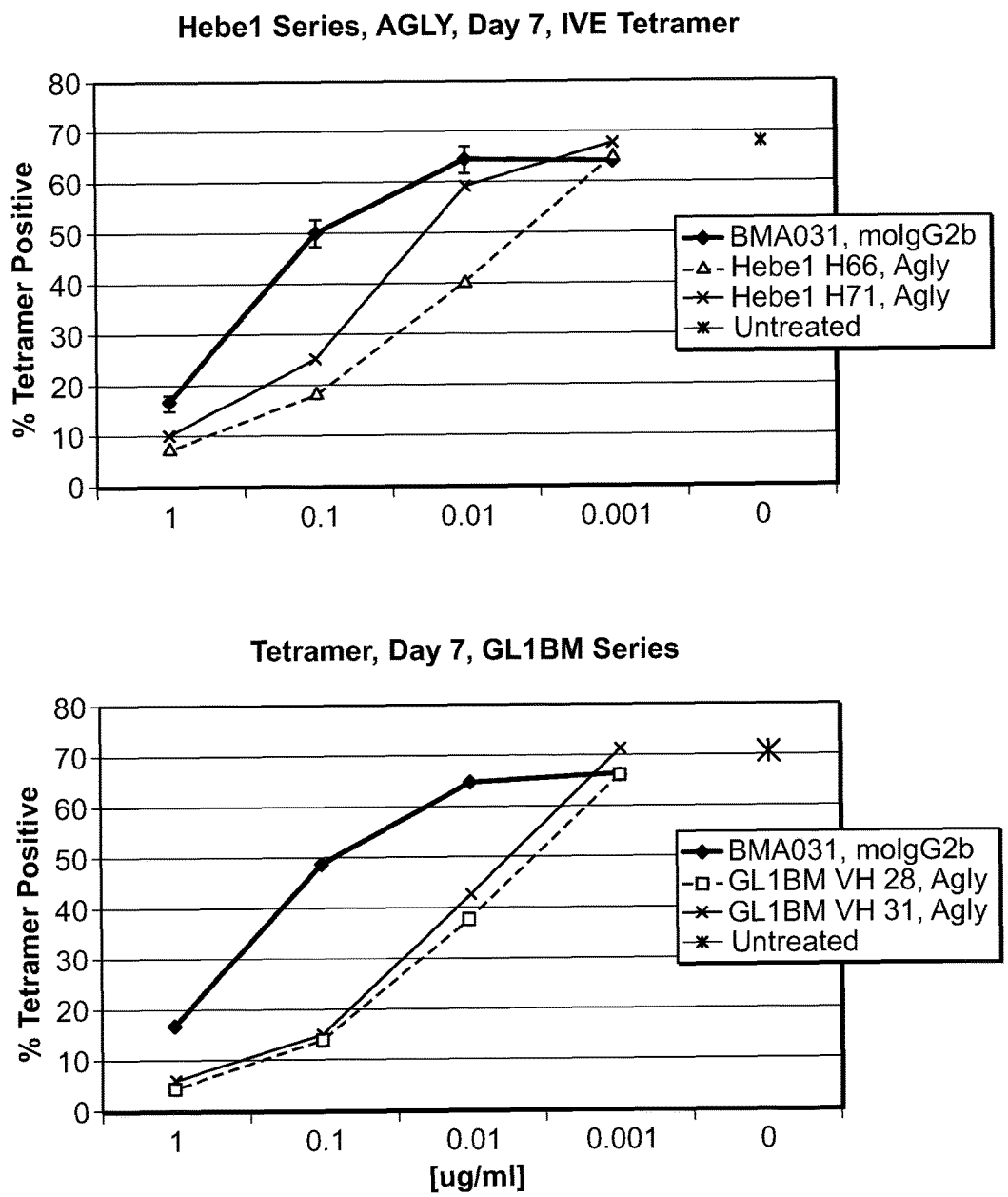

FIG. 11. Antigen positive cells from IVE assay as determined by antigen-specific tetramer binding.

Cells which are antigen-positive (i.e., have been educated within IVE assay) are able to bind to an MHC-tetramer molecule. When the IVE assay was conducted in the presence of antibody which has been able to prevent the education of T cells to antigen, there were fewer cells able to bind to the MHC-tetramer at the end of the assay.

Figure 12:
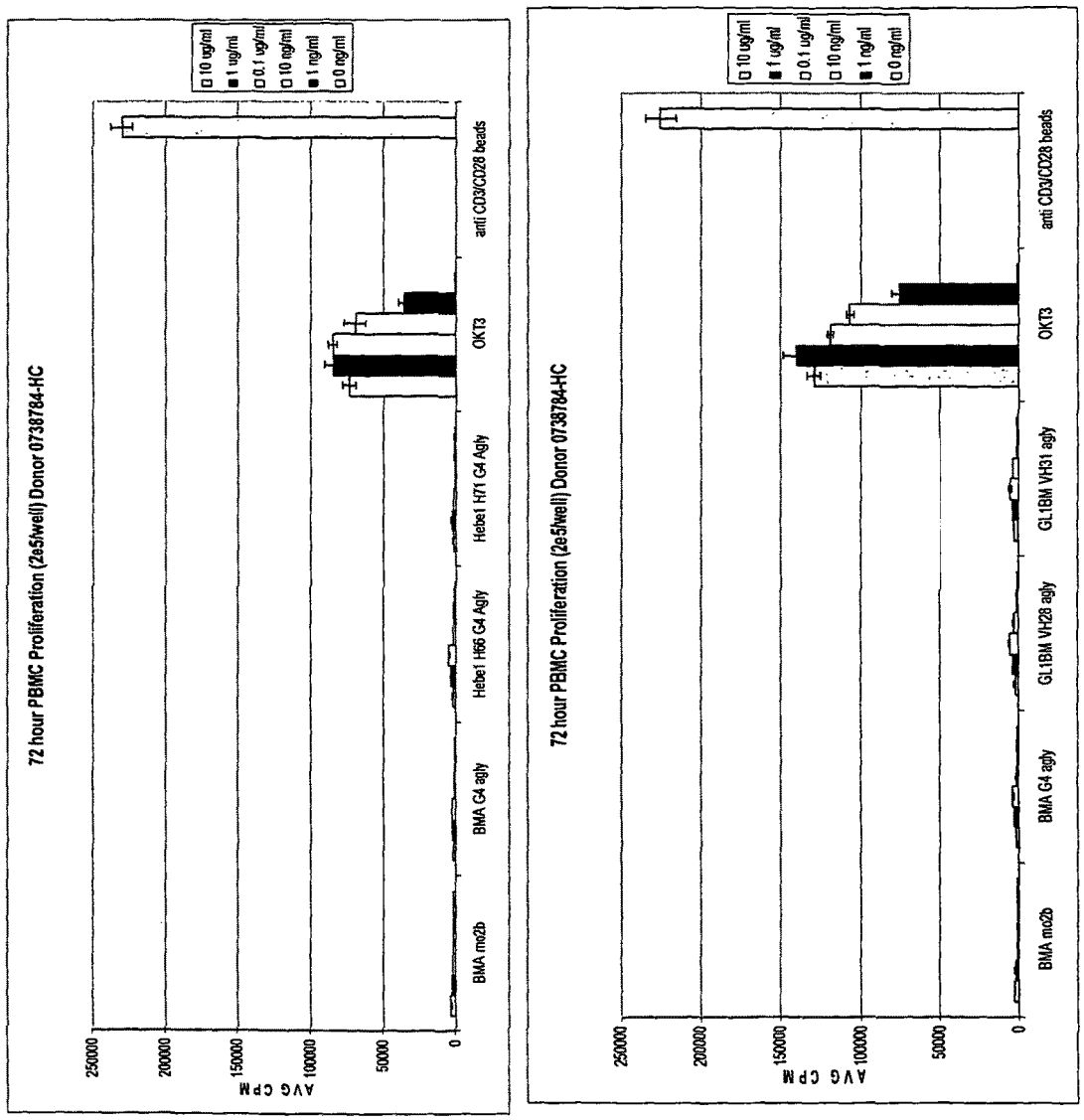

FIG. 12. Proliferation of PBMCs in presence of anti-αβTCR antibodies, OKT3 and stimulatory beads.

The stimulatory activity of OKT3 was not seen in anti-αβTCR antibodies in this comparison.

Figure 13:
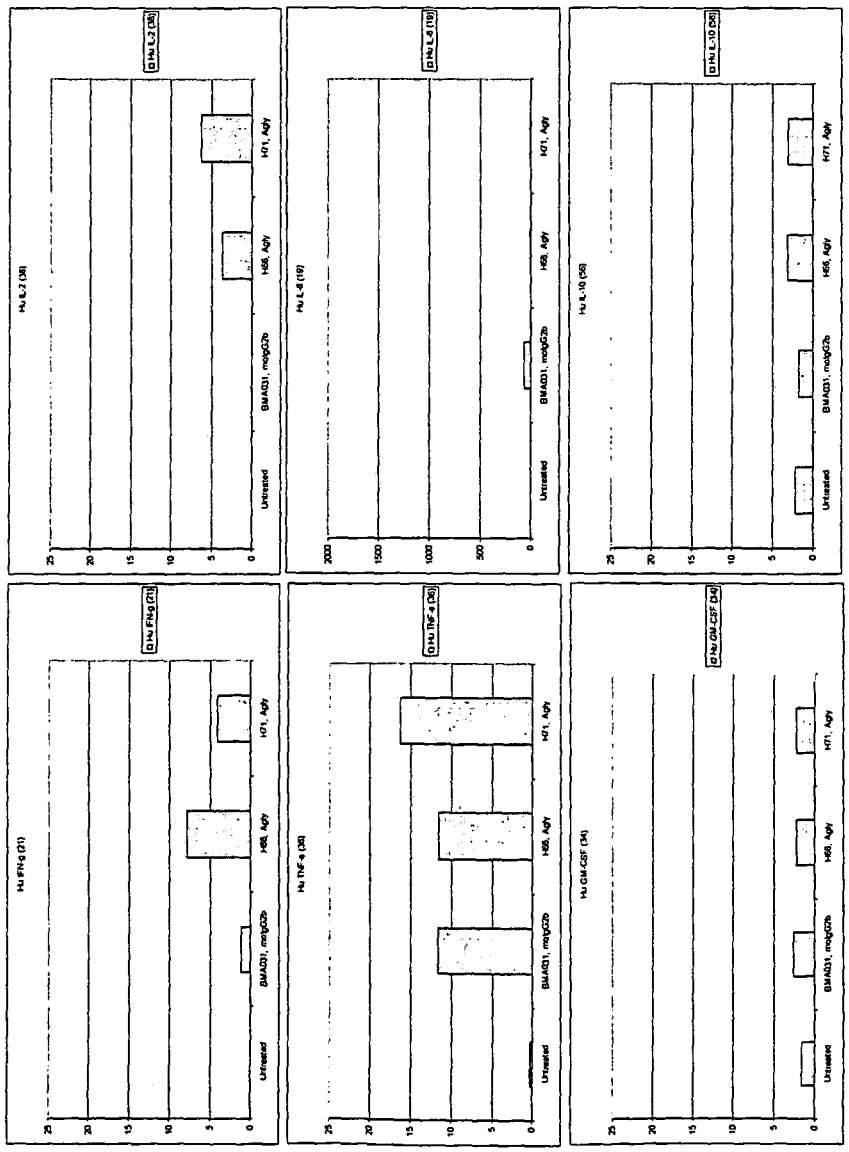

FIG. 13. Cytokine release from PBMCs in presence of anti-αβTCR antibodies.

Cytokine release profile of anti-αβTCR antibodies was similar to the profile demonstrated by BMA031.

Figure 14:
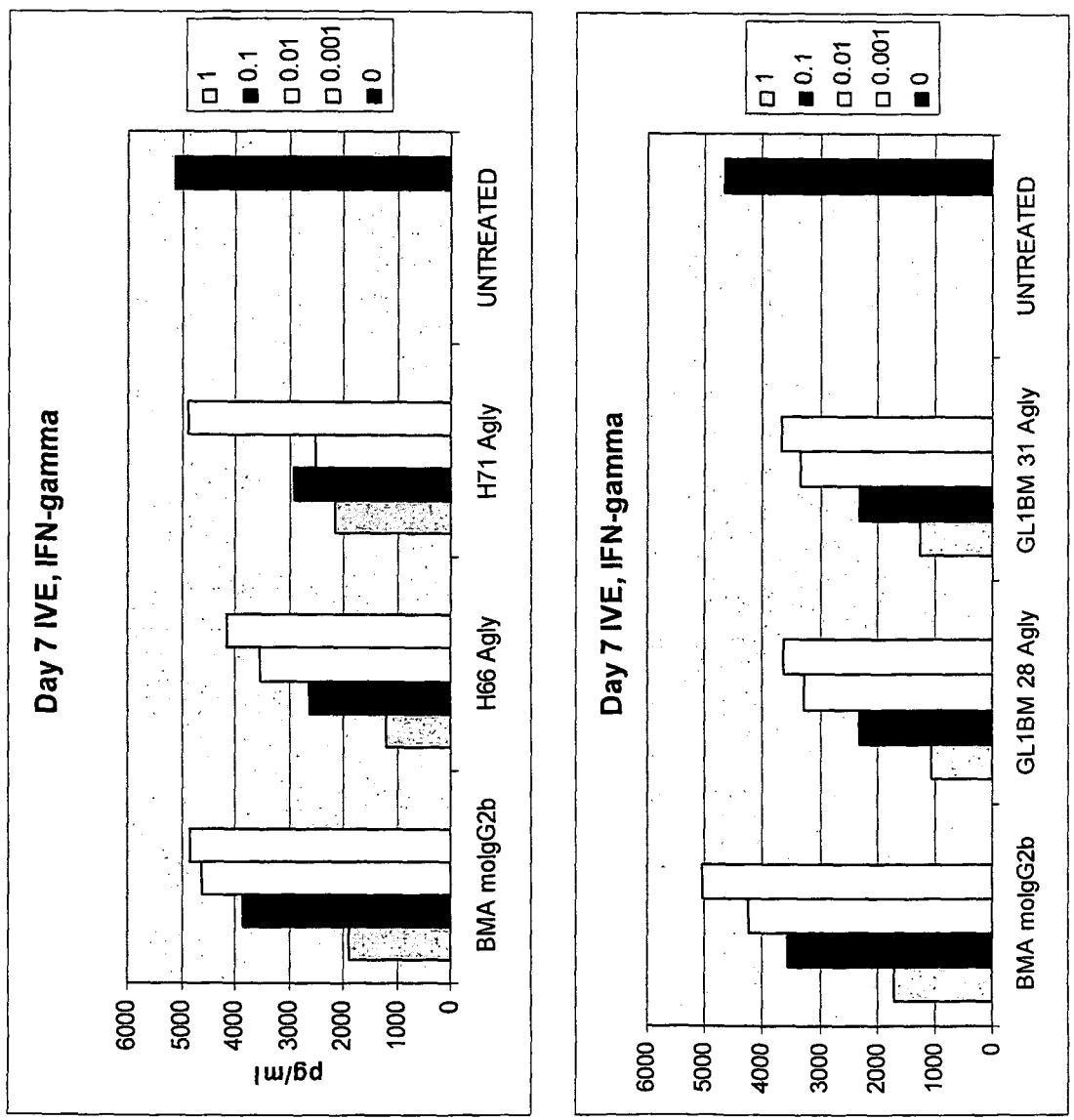

FIG. 14. IFN-gamma release from T cells in IVE assay.

CD8+ T cells were treated with anti-αβTCR antibodies at various concentrations (see FIG. 2, x-axis) and co-cultured with autologous dendritic cells pulsed with the CMV peptide 495-503 (pp65) for seven days in an in vitro education (IVE) assay. IFN-gamma release was measured in this assay.

Figure 15:
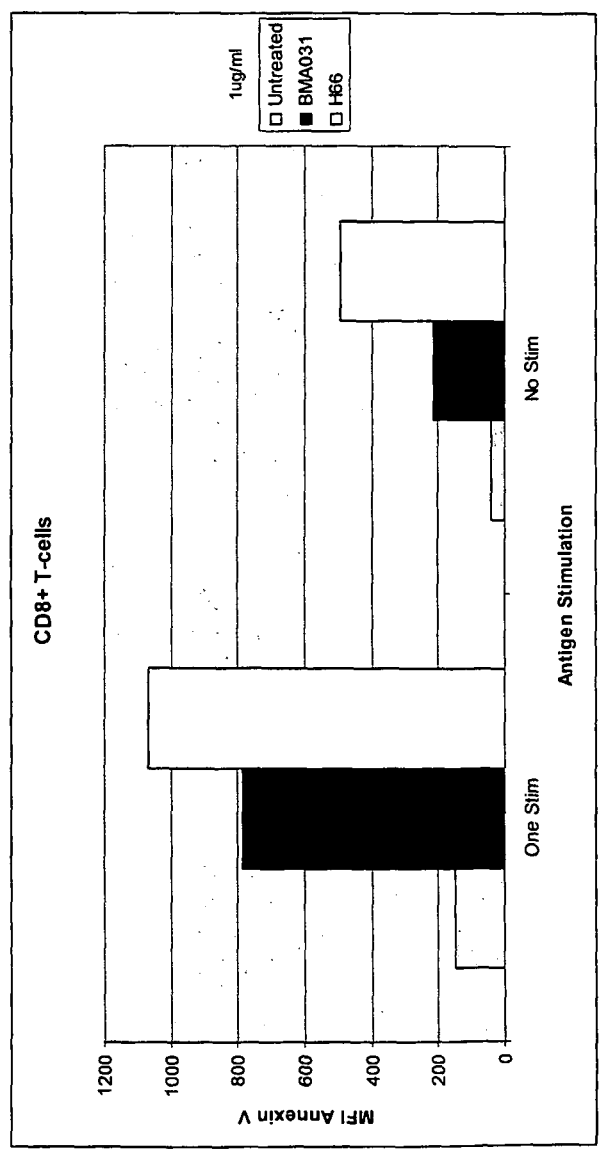

FIG. 15. Activation-induced apoptosis by anti-αβTCR antibodies.

Antigen stimulated CD8+ T cells were induced to apoptosis by binding of anti-αβTCR antibodies BMA031 and HEBE1 H66. The ability of HEBE1 H66 to induce apoptosis was increased compared to BMA031.

Figure 16:
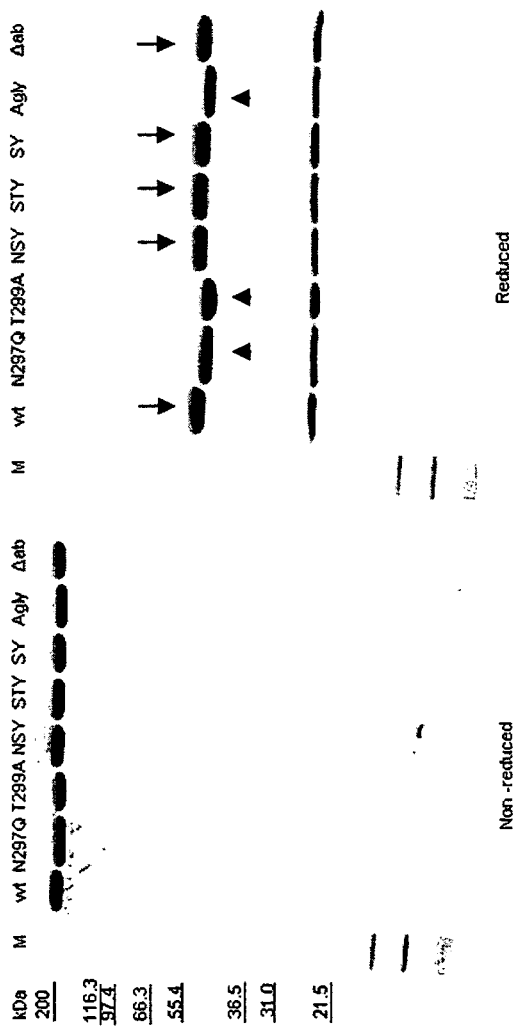

FIG. 16. Isolation of glycosylation mutants and aglycosylated antibodies

Figure 17:
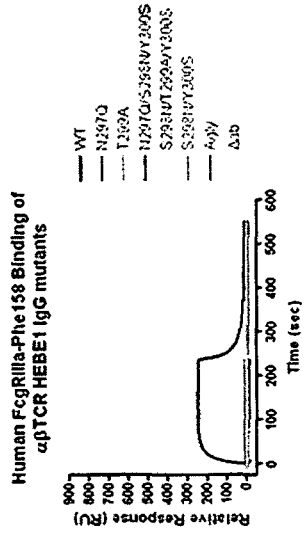
Figure 17:
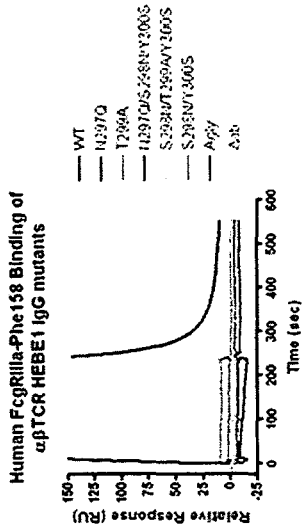
Figure 17:
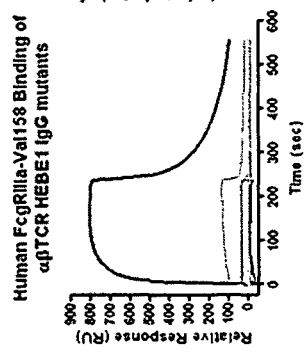
Figure 17:
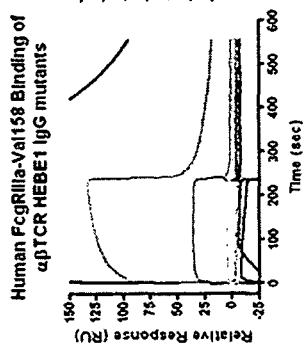

Coomassie-blue stained gel showing expression and purification of glycosylation mutants FIG. 17. Binding of αβTCR antibody mutants to human FcγRIIIa using Biacore.

Biacore was used to assess binding to recombinant human FcγRIIIa (V158 & F158).

Figure 18:
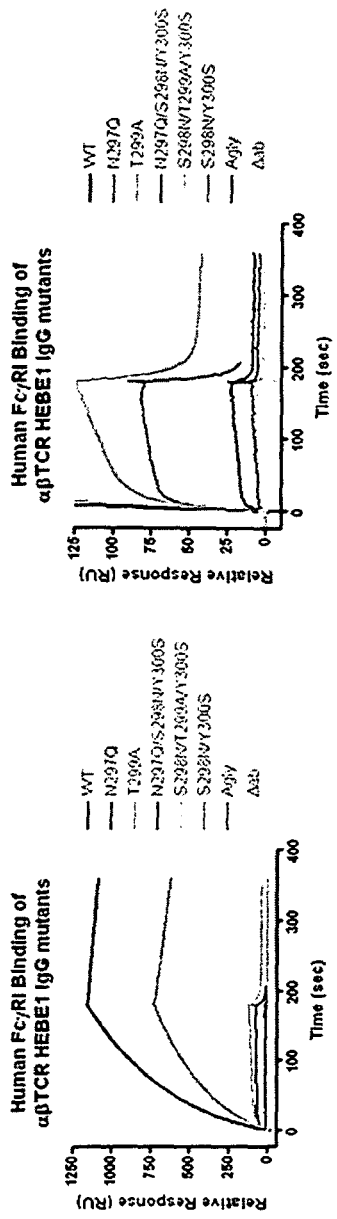

FIG. 18. Binding of αβTCR antibody mutants to human FcγRI using Biacore.

Biacore was used to assess binding to recombinant human and FcγRI.

Figure 19:
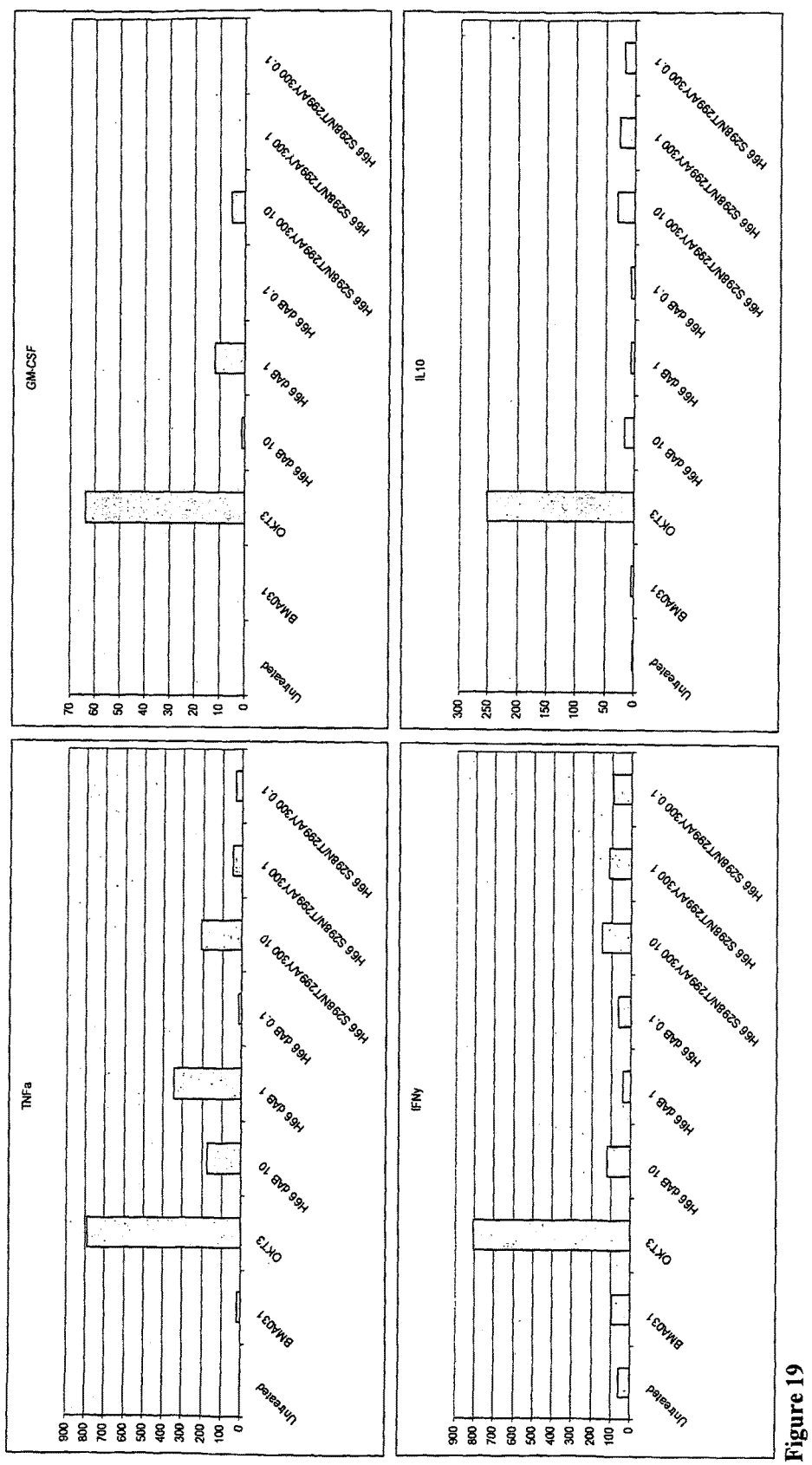

FIG. 19. Cytokine release from PBMCs in presence of glycosylation mutant anti-αβTCR antibodies (day 2).

Cytokine release profile for TNFa, GM-CSF, IFNy and MO of anti-αβTCR antibodies was similar to the profile demonstrated by BMA031 and H66 delta AB.

Figure 20:
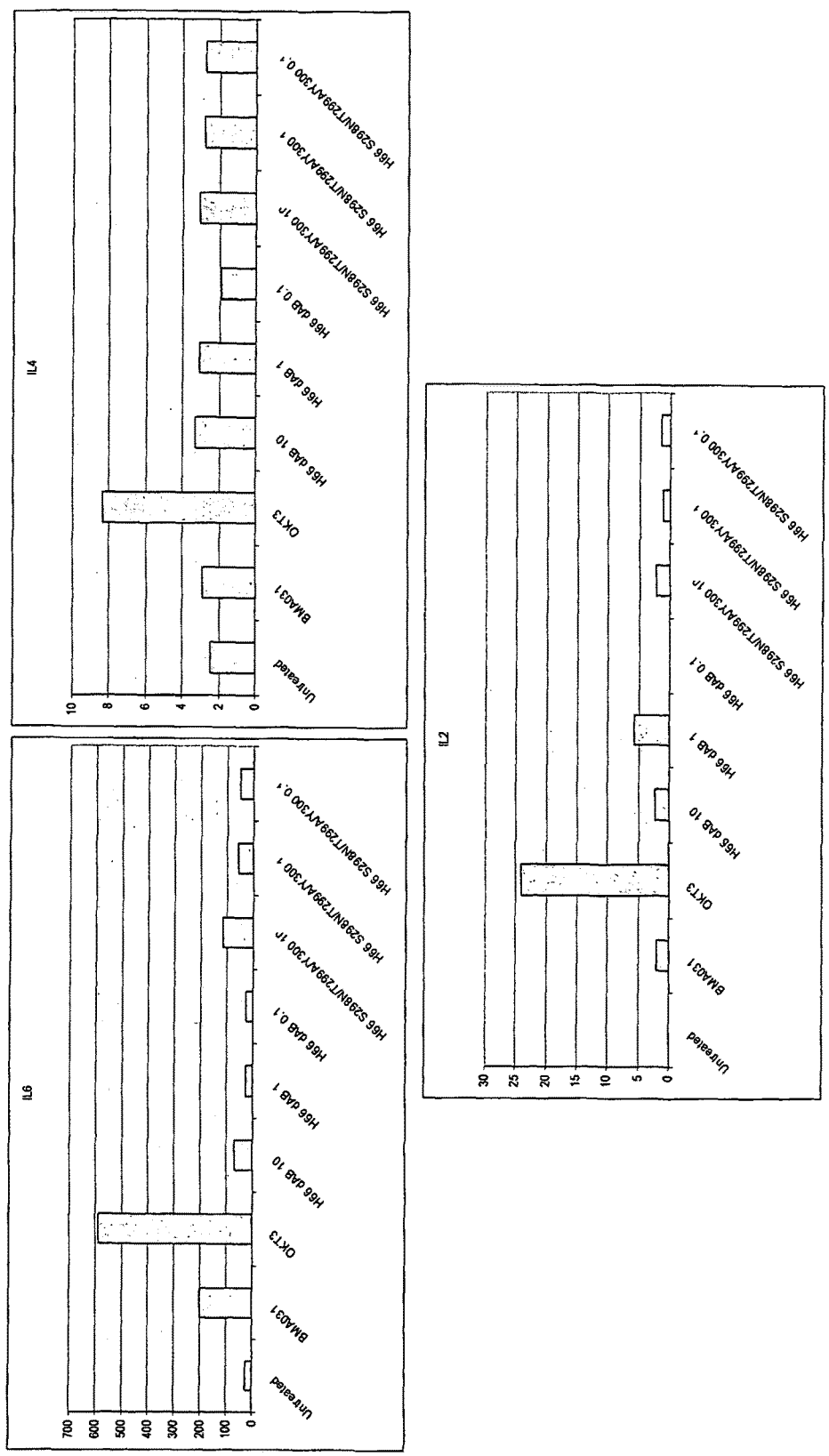

FIG. 20. Cytokine release from PBMCs in presence of glycosylation mutant anti-αβTCR antibodies (day 2).

Cytokine release profile for IL6, IL4 and IL2 of anti-αβTCR antibodies was similar to the profile demonstrated by BMA031 and H66 delta AB.

Figure 21:
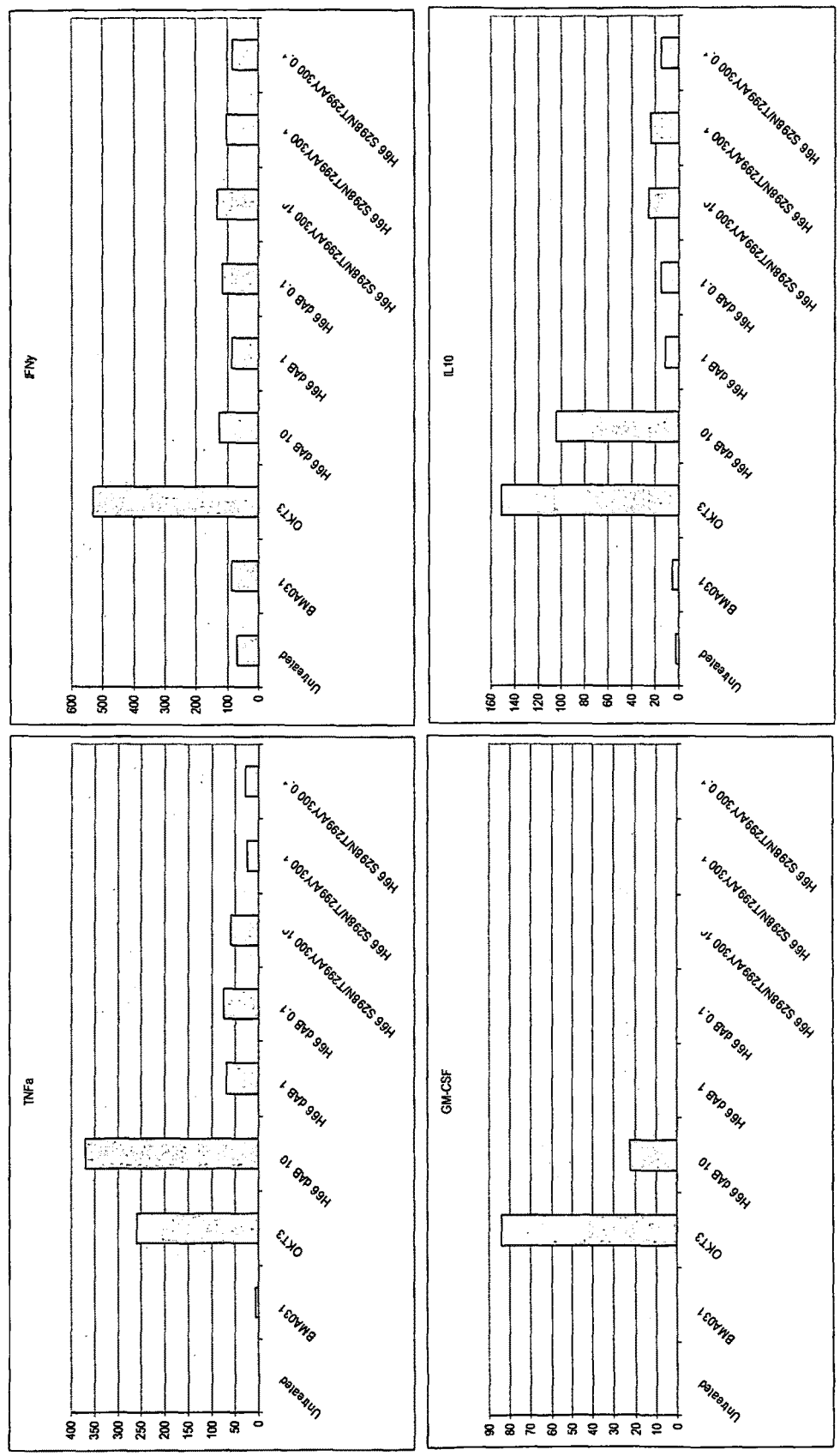

FIG. 21. Cytokine release from PBMCs in presence of glycosylation mutant anti-αβTCR antibodies (day 4).

Cytokine release profile for TNFa, GM-CSF, IFNy and IL10 of anti-αβTCR antibodies was similar to the profile demonstrated by BMA031 and H66 delta AB.

Figure 22:
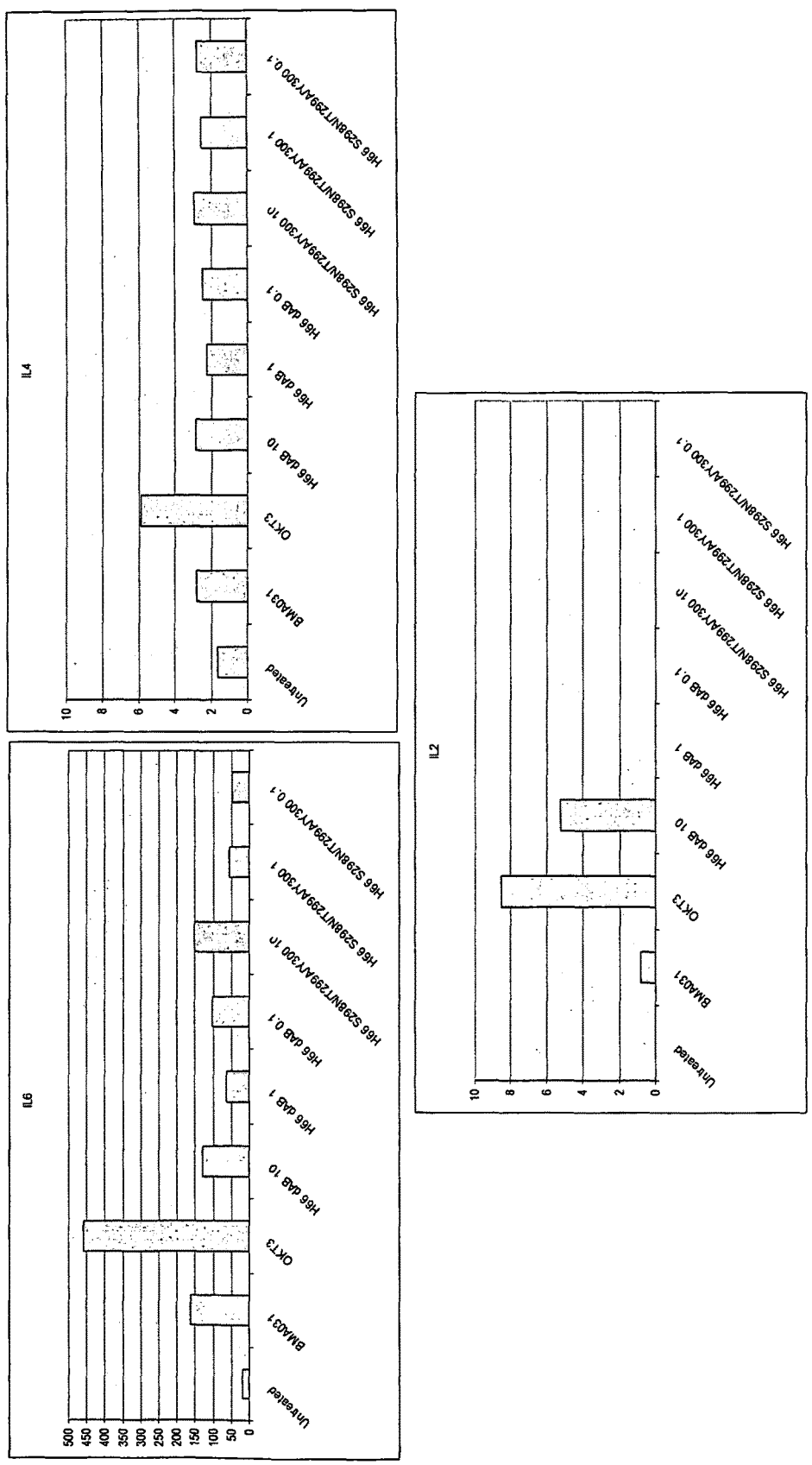

FIG. 22. Cytokine release from PBMCs in presence of glycosylation mutant anti-αβTCR antibodies (day 4).

Cytokine release profile for IL6, IL4 and IL2 of anti-αβTCR antibodies was similar to the profile demonstrated by BMA031 and H66 delta AB.

Figure 23:
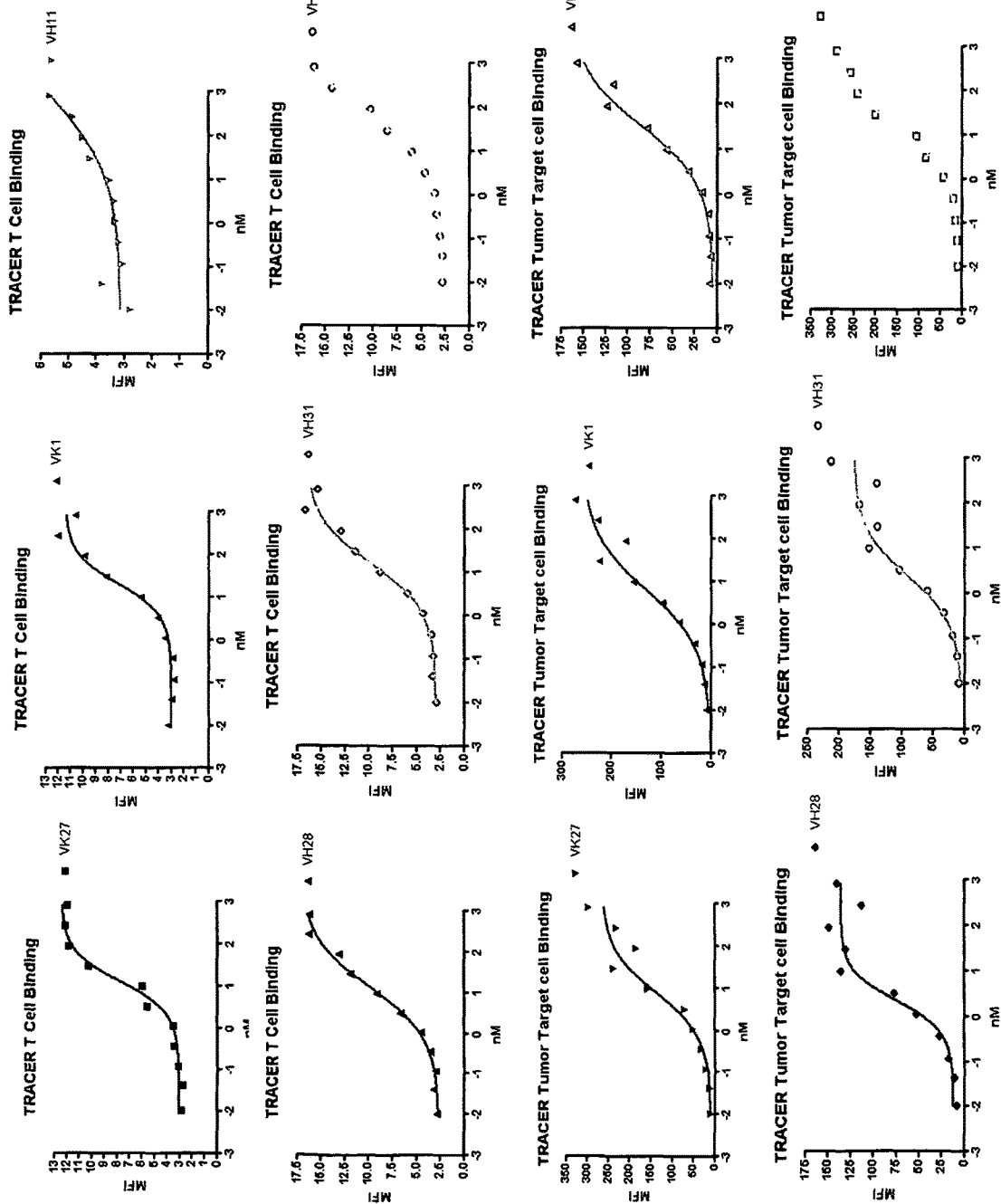

FIG. 23: Binding profiles of TRACERS.

Binding profiles of bi-specific antibodies to both tumor target cells and human T cells assessed by flow cytometery.

Figure 24:
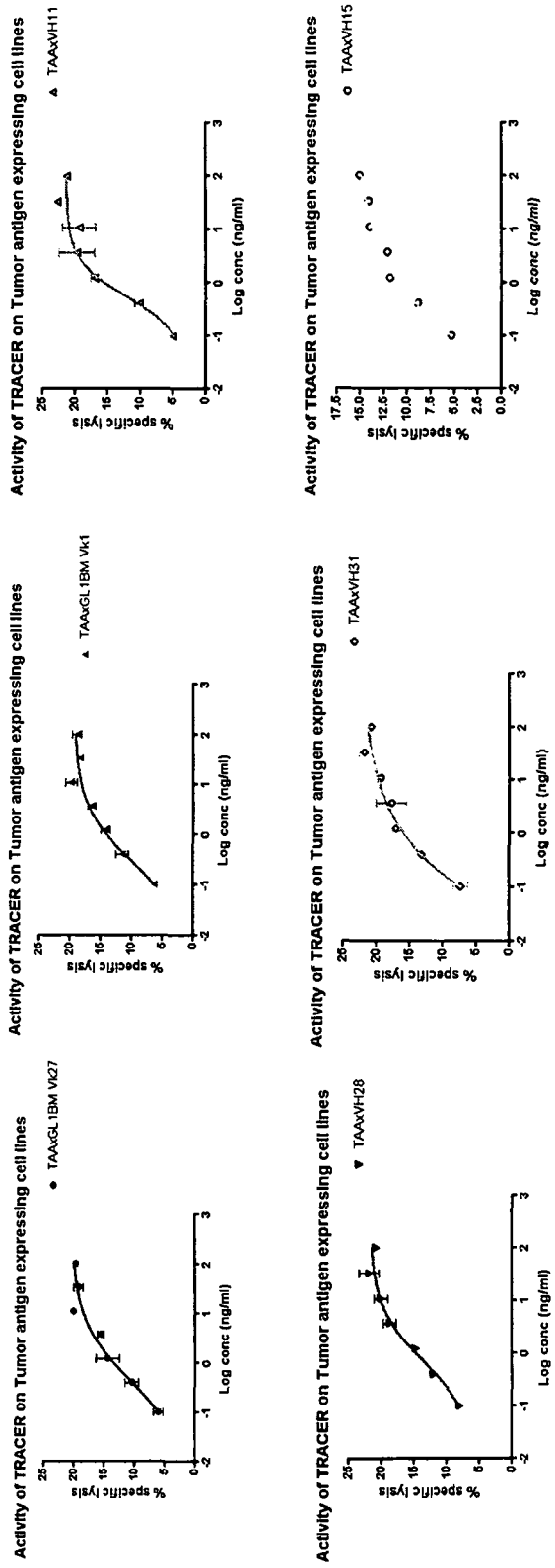

FIG. 24: Cytotoxic activity of different T cell recruitment arms.

Figure 25:
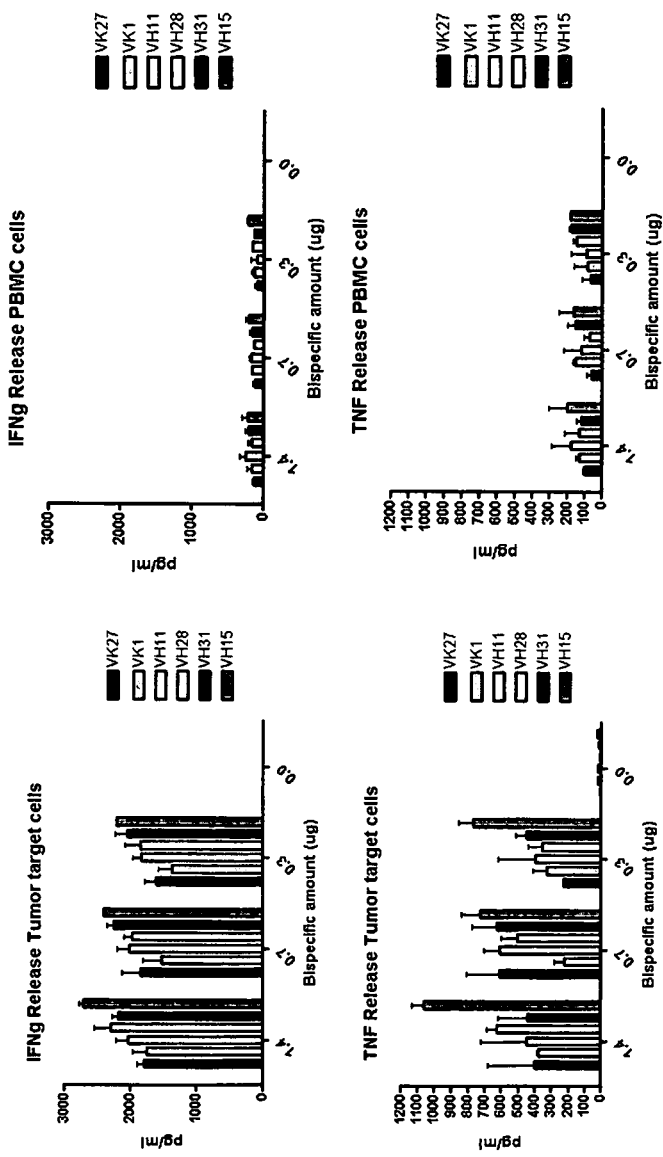

A panel of humanised BMA031 antibodies have been created and from this panel a number of antibodies have been selected which display cytotoxic activity against tumor antigen expressing cell lines FIG. 25: Cytokine release profile of different T cell recruitment arms.

A panel of TRACERs with different T cell recruitment arms show similar cytokine release profiles. Large amounts of cytokines are detected following activation of T cells in the presence of target cells whereas in the presence of only unstimulated human PBMC observed cytokine levels are significantly lower.

Figure 26:
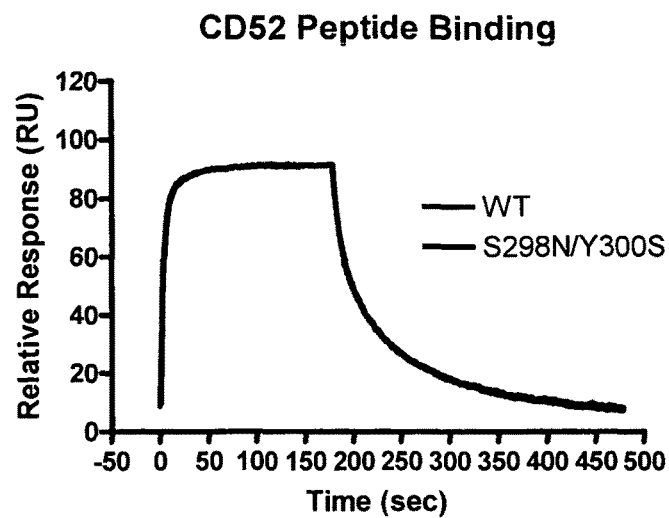
Figure 26:
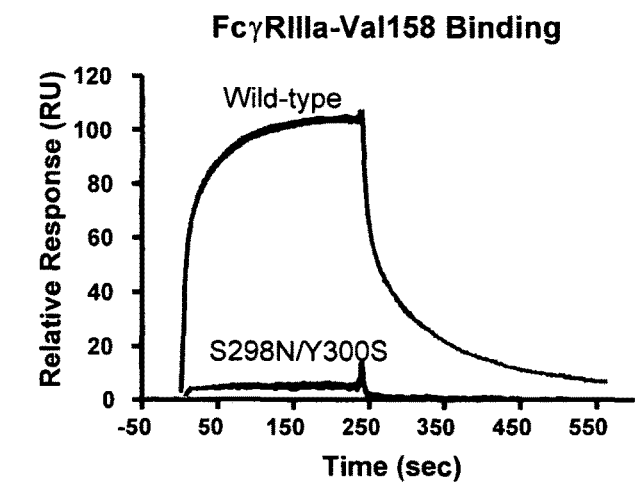
Figure 26:
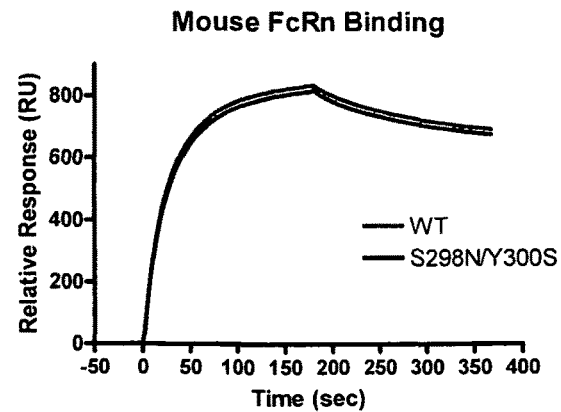

FIG. 26: Binding of CD52 antibody mutants to human FcγRIIIa using Biacore.

Biacore was used to assess binding of modified anti-CD52 to recombinant human FcγRIIIa (V158). Anti-CD52 comprising S298N/Y300S mutations in the Fc domain were used to assess the effector function of the modified molecule. A: binding to CD52 peptide. B: binding to FcγRIIIa (V158). C: control binding to mouse FcRn.

DETAILED DESCRIPTION OF THE INVENTION

Unless otherwise stated, all technical and scientific terms used herein have the same meanings as commonly understood by one of ordinary skill in the art to which this invention belongs. Any methods and materials similar or equivalent to those described herein can be used in the methods or techniques of the present invention. All publications cited herein are incorporated herein by reference in their entirety for the purpose of describing and disclosing the methodologies, reagents, and tools reported in the publications that might be used in connection with the invention.

The methods and techniques of the present application are generally performed according to conventional methods well known in the art and as described in various general and more specific references that are cited and discussed throughout the present specification unless otherwise indicated. See, e.g., Gennaro, A. R., ed. (1990) *Remington's Pharmaceutical Sciences*, 18th ed., Mack Publishing Co.; Hardman, J. G., Limbird, L. E., and Gilman, A. G., eds. (2001) *The Pharmacological Basis of Therapeutics*, 10th ed., McGraw-Hill Co.; Colowick, S. et al., eds., *Methods In Enzymology*, Academic Press, Inc.; Weir, D. M. and Blackwell, C. C., eds. (1986) *Handbook of Experimental Immunology*, Vols. I-IV, Blackwell Scientific Publications; Maniatis, T. et al., eds. (1989) *Molecular Cloning: A Laboratory Manual*, 2nd edition, Vols. I-III, Cold Spring Harbor Laboratory Press; Ausubel, F. M. et al., eds. (1999) *Short Protocols in Molecular Biology*, 4th edition, John Wiley & Sons; Ream et al., eds. (1998) *Molecular Biology Techniques: An Intensive Laboratory Course*, Academic Press; Newton, C. R. and Graham, A., eds. (1997) *PCR (Introduction to Biotechniques Series)*, 2nd ed., Springer-Verlag.

A humanized monoclonal antibody, as referred to herein, is an antibody which is composed of a human antibody framework, into which have been grafted complementarity determining regions (CDRs) from a non-human antibody. Changes in the human acceptor framework may also be made. Procedures for the design and production of humanized antibodies are well known in the art, and have been described, for example, in Cabilly et al., U.S. Pat. No. 4,816,567; Cabilly et al., European Patent Application 0 125 023; Boss et al., U.S. Pat. No. 4,816,397; Boss et al., European Patent Application 0 120 694; Neuberger, M. S. et al., WO 86/01533; Neuberger, M. S. et al., European Patent Application 0 194 276 B1; Winter, U.S. Pat. No. 5,225,539; Winter, European Patent Application 0 239 400; Padlan, E. A. et al., European Patent Application 0 519 596. Further details on antibodies, humanized antibodies, human engineered antibodies, and methods for their preparation can be found in Kontermann, R. and Dübel, S. eds. (2001, 2010) *Antibody Engineering*, 2nd ed., Springer-Verlag, New York, N.Y.

The term "antibody", unless indicated otherwise, is used to refer to entire antibodies as well as antigen-binding fragments of such antibodies. For example, the term encompasses four-chain IgG molecules, as well as antibody fragments.

As used herein, the term "antibody fragments" refers to portions of an intact full-length antibody, for example, as further described below.

Antibodies may be of any class, such as IgG, IgA or IgM; and of any subclass, such as IgG1 or IgG4. Different classes and subclasses of immunoglobulin have different properties, which may be advantageous in different applications. For example, IgG4 antibodies have reduced binding to Fc receptors.

Specificity, in the context of the antibodies described herein, means that the claimed antibody be capable of selectively binding its defined cognate antigen, which is the αβTCR.CD3 complex. The antibodies of the invention bind the αβTCR.CD3 complex expressed on cells.

The human αβTCR/CD3 complex is the T cell receptor complex presented on the surface of T cells. See, Kuhns et al., (2006) *Immunity* 24:133-139. This complex is targeted by the murine monoclonal antibody BMA031 (see, European patent application EP 0 403 156; SEQ ID NOs: 1 and 2).

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain (also called the $V_L$ domain) is a C-terminal portion known as the J region. Within the variable region of the heavy chain (also called the $V_H$ domain), there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3 and FR4, respectively. The locations of CDR and FR regions and a numbering system have been defined by Kabat et al. (Kabat, E. A. et al., *Sequences of Proteins of Immunological Interest*, Fifth Edition, U.S. Department of Health and Human Services, U.S. Government Printing Office (1991), and updates thereof which may be found online). In addition, CDR region boundaries have been further defined by IMGT nomenclature.

Variable regions of antibodies according to the described embodiments may be found in SEQ ID NOs: 5-7 and 12-16, and may be obtained by humanizing BMA031, that is, by transferring the CDRs of BMA031 to a human framework. Two series of humanized antibodies are described; the HEBE1 series, comprising SEQ ID NOs: 5-7, 12 and 13, and the GL1BM series, comprising heavy chain variable regions as shown in SEQ ID NOs: 8, 15 and 16. In both cases, the light chain variable region used is as shown in SEQ ID NO: 14 (GL1BM VK43).

The human frameworks used are IGH3-23 in the case of HEBE1, and IGHV1-3*01 and IGKV3-11*01 in the case of GL1 BM.

Constant regions may be derived from any human antibody constant regions. Variable region genes may be cloned into expression vectors in frame with constant region genes to express heavy and light immunoglobulin chains. Such expression vectors can be transfected into antibody producing host cells for antibody synthesis.

Human antibody variable and constant regions may be derived from sequence databases. For example, immunoglobulin sequences are available in the IMGT/LIGM database (Giudicelli et al., (2006) *Nucleic Acids Res.* 34: (suppl. 1):D781-D784) or VBase (vbase.mrc-cpe.cam.ac.uk).

Aglycosylated antibodies can have extensively modified functionality; see, Boyd et al. (1996) *Mol. Immunol.* 32:1311-1318. A "delta ab" or Δab modification, referred to herein, is an Fc modification as described in Armour et al., (1999) *Eur. J. Immunol.* 29:2613-2624. Techniques for modifying glycosylation of antibody Fc regions are known in the art, and include chemical, enzymatic and mutational means, for example, mutation of the N297 position in the $CH_2$ domain. Techniques for mutating antibody genes for producing aglycosylated IgG molecules are described in Tao and Morrison (1989) *J. Immunol.* 143:2595-2601.

"Nucleic acids" as referred to herein include DNA molecules which encode the antibodies of the invention. Preferred are expression vectors, which are suitable for expressing the antibody genes in a host cell. Expression vectors and host cells for antibody gene expression are known in the art; see, for example, Morrow, K. J. *Genetic Engineering & Biotechnology News* (Jun. 15, 2008) 28(12), and Backliwal, G. et al. (2008) *Nucleic Acids Res.* 36(15):e96-e96.

1. Antibodies

The invention encompasses antigen-binding fragments of the humanized anti-αβTCR antibodies. Fragments of the antibodies are capable of binding the αβTCR.CD3 complex. They encompass Fab, Fab', F(ab')$_2$, and F(v) fragments, or the individual light or heavy chain variable regions or portion thereof. Fragments include, for example, Fab, Fab', F(ab')$_2$, Fv and scFv. These fragments lack the Fc portion of an intact antibody, clear more rapidly from the circulation, and can have less non-specific tissue binding than an intact antibody. These fragments can be produced from intact antibodies using well known methods, for example by proteolytic cleavage with enzymes such as papain (to produce Fab fragments) or pepsin (to produce F(ab')$_2$ fragments).

The antibodies and fragments also encompass single-chain antibody fragments (scFv) that bind to the αβTCR.CD3 complex. An scFv comprises an antibody heavy chain variable region ($V_H$) operably linked to an antibody light chain variable region ($V_L$) wherein the heavy chain variable region and the light chain variable region, together or individually, form a binding site that binds αβTCR. An scFv may comprise a $V_H$ region at the amino-terminal end and a $V_L$ region at the carboxy-terminal end. Alternatively, scFv may comprise a $V_L$ region at the amino-terminal end and a $V_H$ region at the carboxy-terminal end. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv)). An scFv may optionally further comprise a polypeptide linker between the heavy chain variable region and the light chain variable region.

The antibodies and fragments also encompass domain antibody (dAb) fragments as described in Ward, E. S. et al. (1989) *Nature* 341:544-546 which consist of a $V_H$ domain.

The antibodies and fragments also encompass heavy chain antibodies (HCAb). These antibodies are reported to form antigen-binding regions using only heavy chain variable region, in that these functional antibodies are dimers of heavy chains only (referred to as "heavy-chain antibodies" or "HCAbs"). Accordingly, antibodies and fragments may be heavy chain antibodies (HCAb) that specifically bind to the αβTCR.CD3 complex.

The antibodies and fragments also encompass antibodies that are SMIPs or binding domain immunoglobulin fusion proteins specific for αβTCR.CD3 complex. These constructs are single-chain polypeptides comprising antigen-binding domains fused to immunoglobulin domains necessary to carry out antibody effector functions (see, WO 2005/017148).

The antibodies and fragments also encompass diabodies. These are bivalent antibodies in which $V_H$ and $V_L$ domains are expressed on a single polypeptide chain, but using a linker that is too short to allow for pairing between the two domains on the same chain. This forces the domains to pair with complementary domains of another chain and thereby creates two antigen-binding sites (see, for example, WO 93/11161). Diabodies can be bispecific or monospecific.

The antibody or antibody fragment thereof does not cross-react with any target other than the αβTCR.CD3 complex.

The antibody or fragment thereof may be modified in order to increase its serum half-life, for example, by adding molecules—such as PEG or other water soluble polymers, including polysaccharide polymers to increase the half-life.

The antibodies and fragments thereof may be bispecific. For example, bispecific antibodies may resemble single antibodies (or antibody fragments) but have two different antigen binding sites (variable regions). Bispecific antibodies can be produced by various methods—such as chemical techniques, "polydoma" techniques or recombinant DNA techniques. Bispecific antibodies may have binding specificities for at least two different epitopes, at least one of which is the αβTCR.CD3 complex. The other specificity may be selected from any useful or desired specificities including, for example, specificity for human serum albumin for the extension of half-life in vivo.

The use of bi-specific antibodies in the clinic for oncology applications is now becoming reality with the tri-functional Catumaxomab (Removmab®) approved for use in cases of malignant ascites and the bi-specific antibody Blinatumomab now in phase II trials in hematological malignancies. These molecules have in common a binding arm which binds to T cells and a second arm which binds to the tumor target cell which results in T cell mediated lysis of the tumor target. Also in common, these molecules recruit T cells via the CD3 protein located on the cell surface. An alternative to recruitment via CD3 is to make use of the αβ T cell receptor (αβ TCR) which is also expressed on the surface of the cell. Accordingly, antibodies according to the present invention can be used to develop anti-tumor antibodies by combining a specificity for a tumor associated antigen with a specificity for the αβ T cell receptor (αβ TCR).

2. Antibody Production

The amino acid sequences of the variable domains of the antibodies described herein are set forth in SEQ ID NOs: 5-7 and 12-16. Antibody production can be performed by any technique known in the art, including in transgenic organisms such as goats (see, Pollock et al. (1999) *J. Immunol. Methods* 231:147-157), chickens (see, Morrow, K. J. J. (2000) *Genet. Eng. News* 20:1-55), mice (see Pollock et al., supra) or plants (see, Doran, P. M. (2000) *Curr. Opinion Biotechnol.* 11:199-204, Ma. J. K-C. (1998) *Nat. Med.* 4:601-606, Baez, J. et al. (2000) *BioPharm.* 13:50-54, Stoger, E. et al. (2000) *Plant Mol. Biol.* 42:583-590). Antibodies may also be produced by chemical synthesis or by expression of genes encoding the antibodies in host cells.

A polynucleotide encoding the antibody is isolated and inserted into a replicable construct or vector such as a plasmid for further propagation or expression in a host cell. Constructs or vectors (e.g., expression vectors) suitable for the expression of a humanized immunoglobulin according to the described embodiments are available in the art. A variety of vectors are available, including vectors which are maintained in single copy or multiple copies in a host cell, or which become integrated into the host cell's chromosome(s). The constructs or vectors can be introduced into a suitable host cell, and cells which express a humanized immunoglobulin can be produced and maintained in culture. A single vector or multiple vectors can be used for the expression of a humanized immunoglobulin.

Polynucleotides encoding the antibody are readily isolated and sequenced using conventional procedures (e.g., oligonucleotide probes). Vectors that may be used include plasmid, virus, phage, transposons, minichromosomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotides encoding the light and heavy chains may be inserted into separate vectors and introduced (e.g., by transformation, transfection, electroporation or transduction) into the same host cell concurrently or sequentially or, if desired, both the heavy chain and light chain can be inserted into the same vector prior to such introduction.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for prokaryotic and eukaryotic hosts are available. Prokaryotic promoters include lac, tac, T3, T7 promoters for *E. coli;* 3-phosphoglycerate kinase or other glycolytic enzymes e.g., enolase, glyceraldehyde 3-phosphate dehydrogenase, hexokinase, pyruvate decarboxylase, phosphofructokinase, glucose 6 phosphate isomerase, 3-phosphoglycerate mutase and glucokinase. Eukaryotic promoters include inducible yeast promoters such as alcohol dehydrogenase 2, isocytochrome C, acid phosphatase, metallothionein and enzymes responsible for nitrogen metabolism or maltose/galactose utilization; RNA polymerase II promoters including viral promoters such as polyoma, fowlpox and adenoviruses (e.g., adenovirus 2), bovine papilloma virus, avian sarcoma virus, cytomegalovirus (in particular, the immediate early gene promoter), retrovirus, hepatitis B virus, actin, rous sarcoma virus (RSV) promoter and the early or late Simian virus 40 and non-viral promoters such as EF-1 alpha (Mizushima and Nagata (1990) *Nucleic Acids Res.* 18(17):5322). Those of skill in the art will be able to select the appropriate promoter for expressing a humanized antibody or portion thereof.

Where appropriate, e.g., for expression in cells of higher eukaroytes, additional enhancer elements can be included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaryotic cell virus such as SV40 enhancer, cytomegalovirus early promoter enhancer, polyoma enhancer, baculoviral enhancer or murine IgG2a locus (see, WO 04/009823). Whilst such enhancers are often located on the vector at a site upstream to the promoter, they can also be located elsewhere e.g., within the untranslated region or downstream of the polyadenylation signal. The choice and positioning of enhancer may be based upon compatibility with the host cell used for expression.

In addition, the vectors (e.g., expression vectors) may comprise a selectable marker for selection of host cells carrying the vector, and, in the case of a replicable vector, an origin of replication. Genes encoding products which confer antibiotic or drug resistance are common selectable markers and may be used in prokaryotic (e.g., f3-lactamase gene (ampicillin resistance), Tet gene (tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

In eukaryotic systems, polyadenylation and termination signals are operably linked to polynucleotide encoding the antibody of the invention. Such signals are typically placed 3' of the open reading frame. In mammalian systems, non-limiting examples of polyadenylation/termination signals include those derived from growth hormones, elongation factor-1 alpha and viral (e.g., SV40) genes or retroviral long terminal repeats. In yeast systems, non-limiting examples of polydenylation/termination signals include those derived from the phosphoglycerate kinase (PGK) and the alcohol dehydrogenase 1 (ADH) genes. In prokaryotic systems polyadenylation signals are typically not required and it is instead usual to employ shorter and more defined terminator sequences. The choice of polyadenylation/termination sequences may be based upon compatibility with the host cell used for expression. In addition to the above, other features that can be employed to enhance yields include chromatin remodeling elements, introns and host cell specific codon modification. The codon usage of the antibodies of the invention can be modified to accommodate codon bias of the host cell such to augment transcript and/or product yield (e.g., Hoekema, A. et al. (1987) *Mol. Cell Biol.* 7(8):2914-24). The choice of codons may be based upon compatibility with the host cell used for expression.

The invention thus relates to isolated nucleic acid molecules that encode the humanized immunoglobulins, or heavy or light chains, thereof. The invention also relates to isolated nucleic acid molecules that encode an antigen-binding portion of the immunoglobulins and their chains.

The antibodies can be produced, for example, by the expression of one or more recombinant nucleic acids encoding the antibody in a suitable host cell. The host cell can be produced using any suitable method. For example, the expression constructs (e.g., one or more vectors, e.g., a mammalian cell expression vector) described herein can be introduced into a suitable host cell, and the resulting cell can be maintained (e.g., in culture, in an animal, in a plant) under conditions suitable for expression of the construct(s) or vector(s). Host cells can be prokaryotic, including bacterial cells such as *E. coli* (e.g., strain DH5a™) (Invitrogen, Carlsbad, Calif.), PerC6 (Crucell, Leiden, NL), *B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, Sf9 insect cells) (WO 94/126087 (O'Connor)), BTI-TN-5B1-4 (High Five™) insect cells (Invitrogen), mammals (e.g., COS cells, such as COS-1 (ATCC Accession No. CRL-1650) and COS-7 (ATCC Accession No. CRL-1651), CHO (e.g., ATCC Accession No. CRL-9096), CHO DG44 (Urlaub, G. and Chasin, L. A. (1980) *Proc. Natl. Acad. Sci. USA,* 77(7): 4216-4220), 293 (ATCC Accession No. CRL-1573), HeLa (ATCC Accession No. CCL-2), CVI (ATCC Accession No. CCL-70), WOP (Dailey, L., et al. (1985) *J. Virol.,* 54:739-749), 3T3, 293T (Pear, W. S., et al. (1993) *Proc. Natl. Acad. Sci. U.S.A.,* 90:8392-8396), NSO cells, SP2/0 cells, HuT 78 cells, and the like, or plants (e.g., tobacco, lemna (duckweed), and algae). See, for example, Ausubel, F. M. et al., eds. *Current Protocols in Molecular Biology,* Greene Publishing Associates and John Wiley & Sons Inc. (1993). In some embodiments, the host cell is not part of a multicellular organism (e.g., plant or animal), e.g., it is an isolated host cell or is part of a cell culture.

Host cells may be cultured in spinner flasks, shake flasks, roller bottles, wave reactors (e.g., System 1000 from wave-biotech.com) or hollow fibre systems but it is preferred for large scale production that stirred tank reactors or bag reactors (e.g., Wave Biotech, Somerset, N.J. USA) are used particularly for suspension cultures. Stirred tank reactors can be adapted for aeration using e.g., spargers, baffles or low shear impellers. For bubble columns and airlift reactors, direct aeration with air or oxygen bubbles maybe used. Where the host cells are cultured in a serum-free culture medium, the medium can be supplemented with a cell protective agent such as pluronic F-68 to help prevent cell damage as a result of the aeration process. Depending on the host cell characteristics, microcarriers maybe used as growth substrates for anchorage dependent cell lines, or the cells maybe adapted to suspension culture. The culturing of host cells, particularly vertebrate host cells, may utilize a variety of operational modes such as batch, fed-batch, repeated batch processing (see, Drapeau et al. (1994) *Cytotechnology* 15:103-109), extended batch process or perfusion culture. Although recombinantly transformed mammalian host cells may be cultured in serum-containing media such media comprising fetal calf serum (FCS), it is preferred that such host cells are cultured in serum-free media such as disclosed in Keen et al. (1995) *Cytotechnology* 17:153-163, or commercially available media such as ProCHO-CDM or Ultra-CHO™ (Cambrex N.J., USA), supplemented where necessary with an energy source such as glucose and synthetic growth factors such as recombinant insulin. The serum-free culturing of host cells may require that those cells are adapted to grow in serum-free conditions. One adaptation approach is to culture such host cells in serum containing media and repeatedly exchange 80% of the culture medium for the serum-free media so that the host cells learn to adapt in serum-free conditions (see, e.g., Scharfenberg, K. et al. (1995) *Animal Cell Technology: Developments Towards the 21st Century* (Beuvery, E. C. et al., eds), pp.619-623, Kluwer Academic publishers).

Antibodies according to the described embodiments may be secreted into the medium and recovered and purified therefrom using a variety of techniques to provide a degree of purification suitable for the intended use. For example, the use of therapeutic antibodies for the treatment of human patients typically mandates at least 95% purity as determined by reducing SDS-PAGE, more typically 98% or 99% purity, when compared to the culture media comprising the therapeutic antibodies. In the first instance, cell debris from the culture media can be removed using centrifugation followed by a clarification step of the supernatant using e.g., microfiltration, ultrafiltration and/or depth filtration. Alternatively, the antibody can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC) (see, U.S. Pat. No. 5,429,746) are available. In one embodiment, the antibodies, following various clarification steps, are captured using Protein A or G affinity chromatography followed by further chromatography steps such as ion exchange and/or HA chromatography, anion or cation exchange, size exclusion chromatography and ammonium sulphate precipitation. Various virus removal steps may also be employed (e.g., nanofiltration using, e.g., a DV-20 filter). Following these various steps, a purified preparation comprising at least 10 mg/ml or greater, e.g., 100 mg/ml or greater of the antibody of the invention is provided and, therefore, forms another embodiment of the invention. Concentration to 100 mg/ml or greater can be generated by ultracentrifugation. Such preparations are substantially free of aggregated forms of antibodies of the invention.

Bacterial systems are particularly suited for the expression of antibody fragments. Such fragments are localized intracellularly or within the periplasm. Insoluble periplasmic proteins can be extracted and refolded to form active proteins according to methods known to those skilled in the art, see, Sanchez et al. (1999) *J. Biotechnol.* 72:13-20; Cupit, P. M. et al. (1999) *Lett. Appl. Microbiol.* 29:273-277.

The present invention also relates to cells comprising a nucleic acid, e.g., a vector, of the invention (e.g., an expression vector). For example, a nucleic acid (i.e., one or more nucleic acids) encoding the heavy and light chains of a humanized immunoglobulin according to the described embodiments, or a construct (i.e., one or more constructs, e.g., one or more vectors) comprising such nucleic acid(s), can be introduced into a suitable host cell by a method appropriate to the host cell selected (e.g., transformation, transfection, electroporation, infection), with the nucleic acid(s) being, or becoming, operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded humanized antibody can be isolated, for example, from the host cells, culture medium, or milk. This process encompasses expression in a host cell (e.g., a mammary gland cell) of a transgenic animal or plant (e.g., tobacco) (see, e.g., WO 92/03918).

3. Therapeutic Applications

Suppression of T cell activity is desirable in a number of situations in which immunosuppression is warranted, and/or an autoimmune condition occurs. Accordingly, targeting of the αβTCR.CD3 complex is indicated in the treatment of diseases involving an inappropriate or undesired immune response, such as inflammation, autoimmunity, and other conditions involving such mechanisms. In one embodiment, such disease or disorder is an autoimmune and/or inflammatory disease. Examples of such autoimmune and/or inflammatory diseases are Systemic Lupus Erythematosus (SLE), Rheumatoid Arthritis (RA) and inflammatory bowel disease (IBD) (including ulcerative colitis (UC) and Crohn's disease (CD)), multiple sclerosis (MS), scleroderma and type 1 diabetes (T1D), and other diseases and disorders, such as PV (pemphigus vulgaris), psoriasis, atopic dermatitis, celiac disease, Chronic Obstructive Lung disease, Hashimoto's thyroiditis, Graves' disease (thyroid), Sjogren's syndrome, Guillain-barré syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, and vitilgo.

In one embodiment, such disease or disorder is SLE, RA or IBD. In one embodiment, such disease or disorder is MS.

In another embodiment, the antibodies according to the described embodiments are used to aid transplantation by immunosuppressing the subject. Such use alleviates graft-versus-host disease. For a description of existing treatments for graft-versus-host disease, see, e.g., Svennilson, *Bone Marrow Transplantation* (2005) 35:S65-S67, and references cited therein. Advantageously, the antibodies of the invention may be used in combination with other available therapies.

With regard to the treatment of autoimmune diseases, combination therapy may include administration of an antibody of the present invention together with a medicament, which together with the antibody comprises an effective amount for preventing or treating such autoimmune diseases. Where said autoimmune disease is Type 1 diabetes, the combination therapy may encompass one or more of an agent that promotes the growth of pancreatic beta-cells or enhances beta-cell transplantation, such as beta cell growth or survival factors or immunomodulatory antibodies. Where said autoimmune disease is rheumatoid arthritis, said combination therapy may encompass one or more of methotrexate, an anti-TNF-β antibody, a TNF-β receptor-Ig fusion protein, an anti-IL-15 or anti-IL-21 antibody, a non-steroidal anti-inflammatory drug (NSAID), or a disease-modifying anti-rheumatic drug (DMARD). For example, the additional agent may be a biological agent such as an anti-TNF agent (e.g., Enbrel®, infliximab (Remicade®) and adalimumab (Humira®) or rituximab (Rituxan®). Where said autoimmune disease is hematopoietic transplant rejection, hematopoietic growth factor(s) (such as erythropoietin, G-CSF, GM-CSF, IL-3, IL-11, thrombopoietin, etc.) or antimicrobial(s) (such as antibiotic, antiviral, antifungal drugs) may be administered. Where said autoimmune disease is psoriasis, the additional agent may be one or more of tar and derivatives thereof, phototherapy, corticosteroids, Cyclosporine A, vitamin D analogs, methotrexate, p38 mitogen-activated protein kinase (MAPK) inhibitors, as well as biologic agents such as anti-TNF-agents and Rituxan®. Where said autoimmune disease is an inflammatory bowel disease (IBD) such as, for example, Crohn's Disease or ulcerative colitis, the additional agent may be one or more of aminosalicylates, corticosteroids, immunomodulators, antibiotics, or biologic agents such as Remicade® and Humira®.

The combination treatment may be carried out in any way as deemed necessary or convenient by the person skilled in the art and for the purpose of this specification, no limitations with regard to the order, amount, repetition or relative amount of the compounds to be used in combination is contemplated. Accordingly, the antibodies according to the described embodiments may be formulated into pharmaceutical compositions for use in therapy.

4. Pharmaceutical Compositions

In a preferred embodiment, there is provided a pharmaceutical composition comprising an antibody according to the invention, or a ligand or ligands identifiable by an assay method as defined in the previous aspect of the invention. Ligands may be immunoglobulins, peptides, nucleic acids or small molecules, as discussed herein. They are referred to, in the following discussion, as "compounds".

A pharmaceutical composition according to the invention is a composition of matter comprising a compound or compounds capable of modulating T cell activity as an active ingredient. The compound is in the form of any pharmaceutically acceptable salt, or e.g., where appropriate, an analog, free base form, tautomer, enantiomer racemate, or combination thereof. The active ingredients of a pharmaceutical composition comprising the active ingredient according to the invention are contemplated to exhibit therapeutic activity, for example, in the treatment of graft-versus-host disease, when administered in amount which depends on the particular case.

In another embodiment, one or more compounds of the invention may be used in combination with any art recognized compound known to be suitable for treating the particular indication in treating any of the aforementioned conditions. Accordingly, one or more compounds of the invention may be combined with one or more art recognized compounds known to be suitable for treating the foregoing indications such that a convenient, single composition can be administered to the subject. Dosage regima may be adjusted to provide the optimum therapeutic response.

For example, several divided doses may be administered daily or the dose may be proportionally reduced as indicated by the exigencies of the therapeutic situation.

The active ingredient may be administered in a convenient manner such as by the oral, intravenous (where water soluble), intramuscular, subcutaneous, intranasal, intradermal or suppository routes or implanting (e.g., using slow release molecules).

Depending on the route of administration, the active ingredient may be required to be coated in a material to protect said ingredients from the action of enzymes, acids and other natural conditions which may inactivate said ingredient.

In order to administer the active ingredient by means other than parenteral administration, it will be coated by, or administered with, a material to prevent its inactivation. For example, the active ingredient may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water CGF emulsions as well as conventional liposomes.

The active ingredient may also be administered parenterally or intraperitoneally.

Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants.

The prevention of the action of microorganisms can be brought about by various antibacterial and antifungal agents, for example, parabens, chlorobutanol, phenol, sorbic acid, thirmerosal, and the like. In certain cases, it may be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active ingredient in the required amount in the appropriate solvent with several of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Various other materials may be present as coatings or to otherwise modify the physical form of the dosage unit. Of course, any material used in preparing any dosage unit form should be pharmaceutically pure and substantially non-toxic in the amounts employed. In addition, the active ingredient may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

In order to facilitate delivery of peptide compounds, including antibodies, to cells, peptides may be modified in order to improve their ability to cross a cell membrane. For example, U.S. Pat. No. 5,149,782 discloses the use of fusogenic peptides, ion-channel forming peptides, membrane peptides, long-chain fatty acids and other membrane blending agents to increase protein transport across the cell membrane. These and other methods are also described in WO 97/37016 and U.S. Pat. No. 5,108,921, incorporated herein by reference.

In a further aspect there is provided the active ingredient of the invention as hereinbefore defined for use in the treatment of disease either alone or in combination with art recognized compounds known to be suitable for treating the particular indication. Consequently there is provided the use of an active ingredient of the invention for the manufacture of a medicament for the treatment of disease associated with an aberrant immune response.

Moreover, there is provided a method for treating a condition associated with an aberrant immune response, comprising administering to a subject a therapeutically effective amount of a ligand identifiable using an assay method as described above.

The invention is further described, for the purposes of illustration only, in the following examples.

COMPARATIVE EXAMPLE 1

Binding and Biological Activity of EuCIV3 is Decreased Compared with BMA031

Figure 1:
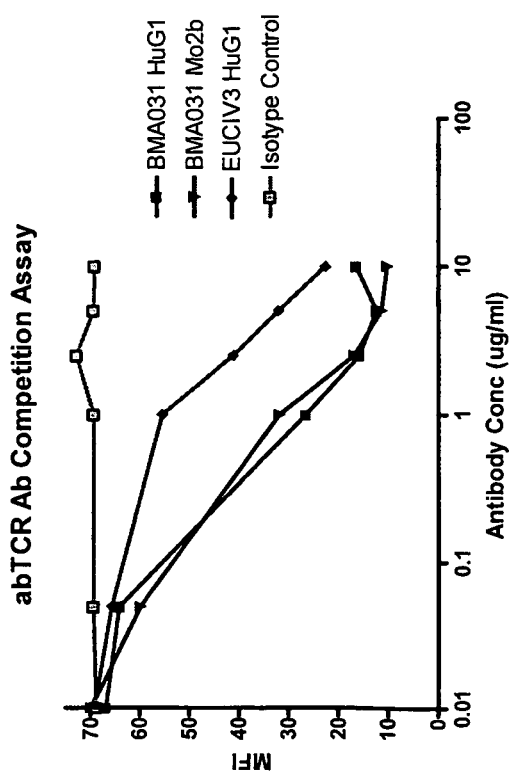
FIG. 1. BMA031 binds more strongly to αβTCR compared to EuCIV3.

Using flow cytometry, we have shown that EuCIV3 is inferior to BMA031 in T cell binding (FIG. 1). In this competition assay, T cells were incubated on ice in the presence of a fixed concentration of directly Phycoerythrin-labeled MoIgG2b-BMA031 (murine competitor) and an increasing concentration of anti-αβTCR antibodies. After 20 minutes incubation, the cells were washed and surface bound directly Phycoerythrin-labeled MoIgG2b-BMA031 was detected by flow cytometry. The BMA031 HuIgG1 chimeric antibody competes much more effectively than EuCIV3.

In order to assess its ability to inhibit T cell activity in vivo, CD8+ T cells were treated with anti-αβTCR antibodies at various concentrations (see, FIG. 2, x-axis) and co-cultured with autologous dendritic cells (DCs) pulsed with the CMV peptide 495-503 (pp65) for seven days in an in vitro education (IVE) assay.

Normal donor aphaeresis products from HLA-A2$^+$ individuals were obtained from HemaCare Corp., Van Nuys, Calif.). PBMC were isolated by centrifugation over Ficoll (GE Healthcare, Piscataway, N.J.). CD8+ T cells were isolated using magnetic beads (Invitrogen, Carlsbad, Calif.) according to the manufacturer's instructions. To generate autologous immature dendritic cells, PBMC were resuspended in RPMI 1640/5% human AB serum (Sigma), plated in triple flasks (Corning) and incubated for more than 2 hours at 37° C./5% $CO_2$. The adherent monocytes were then rinsed with PBS and cultured for 6 days in RPMI 1640/5% human AB serum supplemented with GM-CSF (Immunex, Seattle, Wash.) and IL-4 (PeproTech, Rocky Hill, N.J.). Prior to establishing the T cell/DC co-cultures, the DCs were pulsed with peptides (10 ug/ml) for 4 hours and then matured. Mature dendritic cells were generated by the addition of 50 ng/ml TNF-alpha, 25 ng/ml IL-1β, 10 ng/ml IL-6, 500 ng/ml PGE-2 (PeproTech, Rocky Hill, N.J.) and culturing the dendritic cells for an additional 24 hours. The peptide-pulsed DCs were then added to the previously isolated CD8+ T cells at a T:DC ratio of 10:1. Cultures were immediately fed with IL-2 (100 IU/ml) added to the cultures. The cultures were supplemented with IL-2 (100 IU/ml) on day 4. The bulk cultures were assayed for peptide reactivity in a chromium release assay on day 7.

The graph in FIG. 2 shows lysis data from the chromium release assay, where untreated T cells were successfully educated against pp65 peptide and able to lyse specific targets at >50%. BMA031 inhibited education of these T cells, as they were unable to lyse specific targets in a dose-dependent manner. Humanized antibody EuCIV3 was less potent than BMA031 and was only able to inhibit education at the highest dose.

EXAMPLE 2

Fc Engineering of BMA031 Chimeric Antibodies

In Vitro Profile

We have assessed the in vitro profile of BMA031 in a panel of assays. Table 1 shows the in vitro profile of BMA031. BMA031 is compared to OKT3 in these assays.

In the PBMC proliferation assay, human PBMC were cultured with increasing concentrations of therapeutic antibody for 72 hours, $^3$H-thymidine was added and cells were harvested 18 hours later.

For the T cell depletion/Cytokine Release assay, human PBMC were cultured with increasing concentrations of therapeutic antibody and were analyzed daily for cell counts and viability (Vi-Cell, Beckman Coulter) out to day 7. Cell supernatants were also harvested, stored at −20° C. and analyzed on an 8-plex cytokine panel (Bio-Rad).

BMA031 does not induce: (i) PBMC proliferation; (ii) T cell depletion; (iii) CD25 expression; or (iv) cytokine release. In contrast, OKT3 does induce all of the aforementioned effects. BMA031 and OKT3 are capable of blocking the education of CD8+ cells to peptide in an in vitro education (IVE) assay and are also capable of blocking a mixed lymphocyte reaction (MLR). BMA031 also induces apoptosis of activated T cells (activation-induced cell death; AICD).

Unlike BMA031, a chimeric version of BMA031 (HuIgG1), with wild-type human IgG1 constant region, had an in vitro profile comparable to OKT3 (Table 1). We postulated that FcγR involvement was critical for this change of in vitro profile for HuIgG1 BMA031 compared to BMA031 MoIgG2b. Therefore we made F(ab')$_2$ fragments of BMA031 HuIgG1 and found these to recover the profile of BMA031 MoIgG2b. By Fc engineering we incorporated modifications that removed FcγR binding in mutations known as "delta ab" (Armour et al. (1999) *Eur. J. Immunol.*, 29:2613-2624) and by generating an aglycosylated form of HuIgG4 (N297Q). HuIgG1 delta ab and HuIgG4 agly anti-αβTCR antibodies had the same in vitro profile as BMA031 MoIgG2b (Table 1).

TABLE 1

| | Normal PBMC | | | | | | | Antigen Activated T-cells | | |
|---|---|---|---|---|---|---|---|---|---|---|
| | γδTCR binding | αβTCR binding | FcγR binding | PBMC Proliferation | Depletion | CD25 Expression | Cytokine Release | MLR Inhibition | Apoptosis/ AICD | IVE Inhibition |
| OKT3 | + | + | + | + | + | + | + | + | ND | + |
| BMA031 MoIgG2b | − | + | − | − | − | − | − | + | + | + |
| BMA031 HuIgG1 | − | + | + | + | + | + | + | ND | ND | + |
| BMA031 F(ab)2 | − | + | − | − | − | − | − | ND | ND | + |
| BMA031 Δab HuIgG1 | − | + | − | − | − | − | − | + | + | + |
| HEBE1 Δab HuIgG1 | − | + | − | − | − | − | − | + | + | + |
| HEBE1 IgG4 agly | − | + | − | − | − | − | − | + | + | + |

EXAMPLE 3

Construction of Humanized Antibodies with Improved Binding

We have generated two series of humanized versions of BMA031 called HEBE1 series (IGH3-23) and GL1BM series (IGHV1-3*01 & IGKV3-11*01; see, VBase, vbase.mrc-cpe.cam.ac.uk). Initial grafting of BMA031 heavy chain CDR regions onto IGH3-23 framework regions (see, SEQ ID NOs: 5 and 6) improved the binding of the antibody to the αβTCR as shown by a competition assay (FIG. 3); see, Example 2. However, this improvement did not translate into a functional improvement in the antibody as shown by an IVE assay (FIG. 4).

EXAMPLE 4

Optimization of Humanized Antibodies

The strategy for optimization of the humanized antibodies was based upon mutagenesis and functional screening. Optimization was started with block changes of amino acid residues in one of each of the four framework regions of the variable domains, from mouse to human. Key framework regions were identified in each of the GL1BM HC, GL1BM LC and HEBE1 HC series. Following this identification, individual residues within those framework regions were mutated to human germline residues from the original mouse sequence. Framework residues for which identity with the mouse sequence was found to be important to retaining the binding properties of the antibody were retained as mouse residues. Otherwise, framework residues were changed to match the human germline amino acid sequence. This was continued across the sequence until the minimal number of mouse residues, to retain the original binding properties of the antibody, were identified. See FIG. 5. We have demonstrated that several of the antibodies from these series have an improved binding compared to BMA031 as determined by antibody off-rate from T cells (FIGS. 6, 7 and 8).

For off-rate assays, $10^5$ human T cells were incubated for 30-60 minutes at room temperature in 100 uL full growth media containing 2 ug/mL of the antibodies expressed as HuIgG1-Δab. The cells were then washed, resuspended in 50 uL full growth media and 20 ug/mL of HEBE1 F(ab')$_2$ was added in order to prevent the rebinding of the dissociated candidate antibodies. At the end of this time course assay, the cells were fixed and the level of remaining HuIgG1-Δab antibody bound to the cell surface was measured by flow cytometry via a PE labeled goat anti-HuIgG secondary antibody.

We have also demonstrated that the antibodies are active in preventing the immune response in an IVE (FIGS. 9, 10 and 11) and a MLR assay. In the IVE assay, tetramer binding was used as a quantitative measurement for the IVE. The percentage of cells which were antigen specific was determined by staining the T cells with a directly labeled tetramer that is specific for the educating peptide. Briefly, day 7 CD8+ T cells from the IVE were stained with tetramer by standard flow cytometry staining protocols and analyzed on BD FACSCalibur. In addition, the humanized antibodies demonstrated comparable levels of proliferative potential on PBMCs and cytokine release as compared to BMA031 (FIGS. 12 and 13).

The antibodies also showed an ability to inhibit the release of IFNγ from T cells in an IVE assay (FIG. 14). In addition we have shown that a number of these antibodies have an improved ability to elicit activation-induced cell death (AICD) of activated αβTCR-positive T cells compared to BMA031 (FIG. 15). In the AICD assay, antigen-specific CD8+ T cells were cultured with therapeutic antibody. At 24 hours, 48 hours and 72 hours cells were stained for apoptosis markers Annexin-V and 7-AAD. Cells were also stained with tetramer to track apoptosis with effects on antigen-specific T cells.

In conclusion, we have made significant improvement over previous attempts to humanize BMA031. The discovery of antibodies with an improved off-rate compared to BMA031 is an unexpected finding via this process. This improvement in binding correlates with an improvement in potency to suppress an immune response as demonstrated in the IVE assay (FIGS. 10 and 11). The specificity of the antibodies for αβTCR, the decreased immunogenicity by humanization, the specific apoptosis of activated T cells and the lack of T cell activation upon antibody binding make these antibodies excellent candidates for therapeutic purposes.

EXAMPLE 5

Generation of Fc Mutants for Reduced Effector Function.

Engineered Fc variants was designed and generated where a glycosylation site is introduced at amino acid Ser 298 position, next to the naturally-occurring Asn297 site. The glycosylation at Asn297 was either kept or knocked out by mutations. Mutations and glycosylation results are set forth in Table 2.

TABLE 2

| # | Mutation | Predicted result | Expected Benefit |
|---|---|---|---|
| 1 | N297Q | No glycosylation | Agly Control |
| 2 | T299A | No glycosylation | Agly Control, unknown effector function |

TABLE 2-continued

| # | Mutation | Predicted result | Expected Benefit |
|---|---|---|---|
| 3 | N297Q/S298N/Y300S (NSY) | No glycosylation at 297 but engineered glycosylation site at 298 | Reduced effector function |
| 4 | S298N/T299A/Y300S (STY) | No glycosylation at 297 but engineered glycosylation site at 298 | Reduced effector function |
| 5 | S298N/Y300S (SY) | Two potential glycosylation sites at 297 & 298; Double glycosylation? Mixed glycosylation? | Positive control for reduced effector function |

Mutations were made on the heavy chain of T-cell receptor antibody clone #66 by Quikchange using a pENTR_LIC_IgG1 template. The VH domain of HEBE1 Δab IgG1 #66 was amplified with LIC primers, and cloned into mutated or wild type pENTR_LIC_IgG1 by LIC to create a full-length Ab mutants or wild type. The subcloning was verified with DraIII/XhoI double digest, producing ~1250 bp insert in the successful clones. Those full-length mutants were then cloned into an expression vector, pCEP4(-E+I) Dest, via Gateway cloning. The mutations were then confirmed by DNA sequencing.

Two constructs, HEBE1 Agly IgG4 and HEBE1 Δab IgG1 in pCEP4, were used as controls in HEK293 transfection.

The mutants, wt and controls (Agly and Δab) were transfected into HEK293-EBNA cells in triple-flask for expression. Proteins were purified from 160 ml of conditioned media (CM) with 1 ml HiTrap protein A columns (GE) on multichannel peristaltic pump. Five micrograms of each supernatant were analyzed on 4-20% Tris-Glycine reducing and non-reducing SDS-PAGE (see FIG. 16). The heavy chain of the aglycosylated mutants (N297Q, T299A, and Agly control, is lower (arrow in black), consistent with the loss of the glycans in these antibody. The heavy chains of the engineered glycosylated antibodies (NSY, STY, SY, Δab, and wt control, arrows in red), however, migrate the same way as the wild-type control. This result is consistent with the expected outcome of engineered glycosylation site at 298 positions. SEC-HPLC analysis indicated that all mutants are expressed as monomers.

Glycosylation Analysis by LC-MS.

The Engineered H66 IgG1 Fc variants were partially reduced with 20 mM DTT at 37° C. for 30 min. The samples were analyzed by capillary LC/MS on an Agilent 1100 capillary HPLC system coupling with a QSTAR qq TOF hybrid system (Applied Biosystem). Bayesian protein reconstruct with baseline correction and computer modeling in Analyst QS 1.1 (Applied Bisoystem) was used for data analysis. For mutant S298N/T299A/Y300S H66 antibody lead, one glycosylation site was observed at amino acid 298 with bi-antennary and tri-antennary complex-type glycans detected as the major species, as well as G0F, G1F and G2F.

Binding of αβTCR Antibody Mutants to Human FcγRIIIa and FcγRI using Biacore.

Biacore was used to assess binding to recombinant human FcγRIIIa (V158 & F158) and FcγRI. All 4 flowcells of a CM5 chip were immobilized with anti-HPC4 antibody via the standard amine coupling procedure provided by Biacore. The anti-HPC4 antibody was diluted to 50 μg/mL in 10 mM sodium acetate pH 5.0 for the coupling reaction and injected for 25 min at 5 μL/min. Approximately 12,000 RU of antibody was immobilized to the chip surface. Recombinant human FcγRIIIa-V158 and FcγRIIIa-F158 were diluted to 0.6 μg/mL in binding buffer, HBS-P with 1 mM $CaCl_2$, and injected to flowcells 2 and 4, respectively, for 3 min at 5 μL/min to capture 300-400 RU receptor to the anti-HPC4 chip. In order to distinguish between the low binders, three times more rhFcγRIIIa was captured to the anti-HPC4 surface than usually used in this assay. Flowcells 1 and 3 were used as reference controls. Each antibody was diluted to 200 nM in binding buffer and injected over all 4 flowcells for 4 min, followed by 5 min dissociation in buffer. The surfaces were regenerated with 10 mM EDTA in HBS-EP buffer for 3 min at 20 μL/min.

The results are shown in FIG. 17.

Biacore was also used to compare the FcγRI binding. Anti-tetra His antibody was buffer exchanged into 10 mM sodium acetate pH 4.0 using a Zeba Desalting column and diluted to 25 μg/mL in the acetate buffer for amine coupling. Two flowcells of a CM5 chip were immobilized with ~9000 RU of the anti-Tetra-His antibody after 20 min injection at 5 μL/min. Similar to the previous experiment, ten times more FcγRI was captured to the anti-tetra-His surface in order to compare weak binders. Recombinant human FcγRI was diluted 10 μg/mL in HBS-EP binding buffer and injected to flowcell 2 for 1 min at 5 μL/min to capture ~1000 RU receptor to the anti-tetra-His chip. A single concentration of antibody, 100 nM, was injected for 3 min at 30 μL/min over the captured receptor and control surface. Dissociation was monitored for 3 min. The surface was regeneration with two 30 sec injections of 10 mM glycine pH 2.5 at 20 μL/min.

The results are shown in FIG. 18.

The result suggests very little binding of the glycoengineered mutants to FcγRIIIa or FcγRI. H66 S298N/T299A/Y300S in particular has almost completely abolished binding to both receptors. This mutant was chosen as the lead for detailed characterization.

Stability Characterization Using Circular Dichroism (CD).

The stability of the S298N/T299A/Y300S antibody mutant was monitored by a Far-UV CD thermo melting experiment where the CD signal at 216 nm and 222 nm was monitored as temperature increases that eventually leads to the unfolding of the antibody. The CD spectra were collected on a Jasco 815 spectrophotometer at a protein concentration of approximately 0.5 mg/mL in PBS buffer in a quartz cuvette (Hellma, Inc) with a path length of 10 mm. Temperature was controlled by a thermoelectric peltier (Jasco model AWC100) and was ramped at a rate of 1° C./min from 25-89° C. CD signal and HT voltage were both collected. Data was obtained from 210-260 nm with data intervals of 0.5 nm and at temperature intervals of 1° C. The scanning speed was 50 nm/min and a data pitch of 0.5 nm. A bandwidth of 2.5 nm was used with a sensitivity setting of medium. 4 replicate scans were performed for each sample. The result suggest that both delta AB H66 and the S298N/T299A/Y300S H66 mutant show similar thermal behavior and have the same onset temperature for degradation around 63 C. In other word, the mutant is as stable as the delta AB format.

See FIG. 18.

EXAMPLE 6

Functional Analysis of Fc-Engineered Mutants

PBMC proliferation and cytokine release assays were conducted as set forth in Example 2. Normal donor PBMC were thawed and treated under the following conditions (all in media containing complement):
Untreated
BMA031, moIgG2b 10 ug/ml
OKT3, moIgG2a 10 ug/ml
H66, huIgG1 deltaAB 10 ug/ml, 1 ug/ml and 0.1 ug/ml H66, huIgG1 S298N/T299A/Y300S 10 ug/ml, 1 ug/ml and 0.1 ug/ml Cytokines were harvested at day 2 (D2) and day 4 (D4) for Bioplex Analysis (IL2, IL4, IL6, IL8, IL10, GM-CSF, IFNg, TNFa). Cells were stained at D4 for CD4, CD8, CD25 and abTCR expression.

The results, shown in FIGS. 19-22, demonstrate that H66 S298N/T299A/Y300S behaved similarly to the H66 deltaAB in all cell based assays, showing minimal T-cell activation by CD25 expression; binding to abTCR, although with slightly different kinetics to deltaAB; minimal cytokine release at both D2 and D4 time points; the mutant was in fact superior to deltaAB at D4 in respect of several of the cytokines.

The S298N/T299A/Y300S mutant thus eliminated effector function as effectively as the deltaAB mutation.

EXAMPLE 7

Bispecific Antibodies

Bi-specific molecules were constructed comprised of two single chain antibodies (scFv) linked together via a short amino acid linker whereby one arm is capable of binding a tumor target and the other capable of binding T cells via the αβ TCR. The bispecific molecule is referred to herein as a TRACER (T cell Receptor Activated Cytotoxic EnableR).

The following humanized anti-αβTCR scFv constructs were made:
GL1 BMΔSxVK1
GL1 BMΔSxVK27
GL1BMΔSVH11xVK1
GL1BMΔSVH15xVK1
GL1BMΔSVH28xVK43
GL1BMΔSVH31xVK43

The sequences of the heavy and light chains are set forth in SEQ ID nos 14-16 and 20-24

Characterization of these molecules comprised an assessment of binding to tumor target and T cells, in vitro cytotoxic activity and cytokine release profile in the presence and absence of tumor target cells.

The binding profile assessed by flow cytometery shows that anti-αβ TCR bi-specific antibodies are able to bind both the tumor target cell line and T cells. See FIG. 23.

In vitro cytotoxic activity measured by flow cytometery shows that T cells recruited via anti-αβ TCR bi-specific antibody are capable of inducing T cell mediated lysis. See FIG. 24.

Analysis of the cytokine release profile has shown that upon binding of both arms of the bi-specific antibody there is a high level of TH1/TH2 cytokine release from the T cells which is not seen in the absence of target cells. Taken together this mechanism of action shows a similar profile to that of the CD3 based bispecifics described in the literature.

EXAMPLE 8

Preparation and Characterization of an Engineered Fc Variant in Anti-CD52 Antibody In order to test the generality of the applicability of the Fc mutations described herein, glycosylation mutant S298N/Y300S was also prepared in an anti-CD52 antibody (clone 2C3) to see whether the effector function modulation with the loss of FcγRIII binding applies to a different antibody backbone. S298N/Y300S 2C3 variant DNA was prepared by quick change mutagenesis. The protein was purified from conditioned media after HEK293 transient transfection. Anti-CD52 2C3 wild-type antibody was produced in parallel as a control. Biacore was used to characterize the antigen-binding, FcγRIII, and binding properties of the purified antibodies (see FIG. 26).

The S298N/Y300S 2C3 variant binds to CD52 peptide tightly and the binding sensorgram is undistinguishable with the wild-type control, suggesting that this mutation on the Fc domain does not affect its antigen binding (FIG. 26A).

To assay Fc effector function, FcγRIII receptor (Val158) was used in binding studies. The mutant and wild-type control antibody were diluted to 200 nM and injected to HPC4-tag captured FcγRIIIa. FcγRIII binding is almost undetectable for the S298N/Y300S mutant, which indicates loss of effector function with this variant (FIG. 26B). The mutant also binds to FcRn receptor with the same affinity as the wild-type antibody control so we expect no change in its circulation half-life or other pharmacokinetic properties. (see FIG. 26C). We conclude that the S298N/Y300S mutation is applicable to antibodies in general, to reduce or eliminate undesired Fc effector function, for example through engagement of human Fcγ receptors.

The invention claimed is:

1. A humanized monoclonal antibody specific for the human αβTCR/CD3 complex which comprises a heavy chain variable region comprising an amino acid sequence selected from the group consisting of SEQ ID NOs: 7, 12, 13, 15 and 16, a light chain variable region comprising the amino acid sequence set forth as SEQ ID NO 14, and a constant region of human origin, wherein the constant region comprises an Fc modification with a modified glycosylation pattern that reduces Fcγ receptor binding, wherein the Fc modification is selected from the group consisting of N297Q/S298N/Y300S, S298N/T299A/Y300S, and S298N/Y300S.

2. The humanized monoclonal antibody of claim 1, wherein the heavy chain variable region amino acid sequence is selected from the group consisting of the amino acid sequences set forth as SEQ ID NO: 7, SEQ ID NO: 12 and SEQ ID NO: 13.

3. The humanized monoclonal antibody of claim 1, wherein the heavy chain variable region comprises an amino acid sequence selected from the group consisting of SEQ ID NO: 15 and SEQ ID NO: 16.

4. The humanized antibody of claim 1, wherein the heavy chain variable region comprises the amino acid sequence set forth as SEQ ID NO: 16.

5. The humanized antibody of claim 1, wherein the heavy chain variable region comprises the amino acid sequence set forth as SEQ ID NO: 15.

6. The humanized antibody of claim 1, wherein the Fcγ receptor is one or more receptor selected from the group consisting of FcγRIIIa and FcγRI.

7. A pharmaceutical composition, comprising the antibody of claim 1 and a pharmaceutically acceptable carrier or diluent.

8. A pharmaceutical composition, comprising the antibody of claim 4 and a pharmaceutically acceptable carrier or diluent.

9. A pharmaceutical composition, comprising the antibody of claim 5 and a pharmaceutically acceptable carrier or diluent.

10. The humanized monoclonal antibody of claim 1, wherein the Fc modification is N297Q/S298N/Y300S.

11. The humanized monoclonal antibody of claim 1, wherein the Fc modification is S298N/T299A/Y300S.

12. The humanized monoclonal antibody of claim 1, wherein the Fc modification is S298N/Y300S.

* * * * *